(12) United States Patent
Maru et al.

(10) Patent No.: US 11,179,424 B2
(45) Date of Patent: Nov. 23, 2021

(54) HYALURONIC ACID PRODUCTION PROMOTING AGENT

(71) Applicant: Pharma Foods International Co., Ltd., Kyoto (JP)

(72) Inventors: Isafumi Maru, Kyoto (JP); Ji-Yeong An, Kyoto (JP); Sayuri Tanaka, Kyoto (JP); Maya Sakashita, Kyoto (JP); Seiyu Harada, Kyoto (JP); Kazuya Watabe, Kyoto (JP); Masayoshi Aosasa, Kyoto (JP); Mujo Kim, Kyoto (JP); Toshio Nakamura, Kyoto (JP); Utano Nakamura, Kyoto (JP); Hiroaki Iitsuka, Kyoto (JP)

(73) Assignee: Pharma Foods International Co., Ltd., Kyoto (JP)

( * ) Notice: Subject to any disclaimer, the term of this patent is extended or adjusted under 35 U.S.C. 154(b) by 617 days.

(21) Appl. No.: 15/670,918

(22) Filed: Aug. 7, 2017

(65) Prior Publication Data
US 2018/0036350 A1  Feb. 8, 2018

Related U.S. Application Data

(63) Continuation-in-part of application No. PCT/JP2015/084852, filed on Dec. 11, 2015.

(30) Foreign Application Priority Data

Feb. 9, 2015  (JP) .............................. JP2015-023507

(51) Int. Cl.
| | | |
|---|---|---|
| A61K 38/05 | (2006.01) | |
| A61K 35/57 | (2015.01) | |
| A23C 19/093 | (2006.01) | |
| A61K 38/01 | (2006.01) | |
| A23C 9/13 | (2006.01) | |
| A23L 2/60 | (2006.01) | |
| A61K 9/20 | (2006.01) | |
| A61K 9/48 | (2006.01) | |
| A61K 8/73 | (2006.01) | |
| A23L 2/56 | (2006.01) | |
| A23L 33/18 | (2016.01) | |
| A61K 8/65 | (2006.01) | |
| A23L 33/00 | (2016.01) | |
| A23C 9/123 | (2006.01) | |
| A23C 19/00 | (2006.01) | |
| A23L 2/52 | (2006.01) | |
| A61K 8/60 | (2006.01) | |
| A61K 8/64 | (2006.01) | |
| A61K 8/98 | (2006.01) | |
| A61K 31/7004 | (2006.01) | |
| A61Q 19/00 | (2006.01) | |
| A61Q 19/08 | (2006.01) | |

(52) U.S. Cl.
CPC .............. *A61K 35/57* (2013.01); *A23C 9/123* (2013.01); *A23C 9/1322* (2013.01); *A23C 19/00* (2013.01); *A23C 19/093* (2013.01); *A23L 2/52* (2013.01); *A23L 2/56* (2013.01); *A23L 2/60* (2013.01); *A23L 33/18* (2016.08); *A23L 33/30* (2016.08); *A61K 8/60* (2013.01); *A61K 8/64* (2013.01); *A61K 8/65* (2013.01); *A61K 8/735* (2013.01); *A61K 8/981* (2013.01); *A61K 9/2068* (2013.01); *A61K 9/4875* (2013.01); *A61K 31/7004* (2013.01); *A61K 38/012* (2013.01); *A61K 38/014* (2013.01); *A61K 38/05* (2013.01); *A61Q 19/007* (2013.01); *A61Q 19/08* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2006/0019892 A1* | 1/2006 | Mari ........................ | C07K 7/06 514/18.3 |
| 2007/0281009 A1 | 12/2007 | Kamisono et al. | |
| 2011/0160137 A1* | 6/2011 | Kim ........................ | A61K 8/365 514/17.2 |
| 2012/0040055 A1* | 2/2012 | Ohara ...................... | A23J 3/342 426/63 |
| 2016/0082087 A1* | 3/2016 | Koizumi ................. | A61Q 19/02 424/62 |

FOREIGN PATENT DOCUMENTS

| | | |
|---|---|---|
| JP | 2001-2551 A | 1/2001 |
| JP | 2001-31699 A | 2/2001 |
| JP | 2003-48850 A | 2/2003 |

(Continued)

OTHER PUBLICATIONS

Imhof, Arthritis & Rheumatism, vol. 63, No. 8, Aug. 2011, pp. 2352-2362. (Year: 2011).*

(Continued)

*Primary Examiner* — Satyanarayana R Gudibande
(74) *Attorney, Agent, or Firm* — Knobbe, Martens, Olson & Bear, LLP

(57) ABSTRACT

An agent of the present invention comprising poultry feet or a processed product thereof, preferably a hydrolysate of an extract of poultry feet, promotes hyaluronic acid production, thereby exhibiting excellent effects of preventing or treating a joint disorder, improving skin dryness, wrinkles or skin tension, moisturizing the skin, etc. The agent is thus useful as a medicament, a quasi-drug, a cosmetic product, a food product or an animal feed.

2 Claims, 9 Drawing Sheets

(56) References Cited

FOREIGN PATENT DOCUMENTS

| | | |
|---|---|---|
| JP | 4336486 | 4/2004 |
| JP | 2009-269929 A | 11/2009 |
| JP | 2011-98983 A | 5/2011 |
| JP | 2012-62279 A | 3/2012 |
| JP | 2014-210766 A | 11/2014 |
| WO | WO-8901780 A1 * 3/1989 ............ A61P 25/04 |
| WO | WO 02/098449 A1 | 12/2002 |
| WO | WO 2014/007318 A1 | 1/2014 |

OTHER PUBLICATIONS

Liu, Pflugers Arch—Eur J Physiol (2013) 465:1671-1685 (Year: 2013).*

Imhof—STNext-Search-notes.pdf, 2 pages, 2020 (Year: 2020).*

Maru, Isafumi et al., "Keisoku Yurai Hyaluronan Sansei Sokushin Busshitsu (HA-II) no Hiza Nankotsu ni Oyobosu Koka" Proceedings (online) of the Annual Meeting of Japan Society for Bioscience, Biotechnology, and Agrochemistry, Mar. 5, 2015, vol. 2015.

Maru, Isafumi et al., "Locomotive Syndrome Taio no Kinosei Sozai—Sarcopenia, Frailty o Chushin ni~ Keisoku ni Himerareta Hiza Nankotsu Hyaluronan Sansei sokushin Sozai 'HAS-II'" Food Style 21, Jun. 2015, pp. 52-55, vol. 19, No. 6.

Ohara, Hiroki et al., "Collagen-derived dipeptide, proline-hydroxyproline, stimulates cell proliferation and hyaluronic acid synthesis in cultured human dermal fibroblasts" Journal of Dermatology, 2010, pp. 330-338, vol. 37.

Taguchi, Yasuki et al., "Sozai to shite no Chikusan-butsu Nikuyodori (Broiler) o Riyo shita Kinosei Shokuhin Sozai no Kaihatsu" Food Chemicals, 2003, pp. 27-31, vol. 19, No. 5.

Watabe, Kazuya et al., "Keisoku Yurai Hyaluronan Sansei Sokushin Busshitsu (HA-II) no Kaihatsu" Proceedings (online) of the Annual Meeting of Japan Society for Bioscience, Biotechnology, and Agrochemistry(Web), Mar. 2015, vol. 2015.

Japan Society for Bioscience, Biotechnology, and Agrochemistry 2015 Nendo Taikai Luncheon Seminar—Jan. 27, 2015.

We! PFI, published by Pharma Foods International Co., Ltd., Jan. 2015, vol. 13, p. 11.

International Preliminary Report on Patentability for PCT/JP2015/084852 dated Aug. 15, 2017.

International Search Report for PCT/JP2015/084852 dated Jan. 26, 2016.

Morphine: Uses, Dosage, Side Effects, Warnings—Drugs.com https://www.drugs.com/morphine.html (last updated Nov. 4, 2019).

* cited by examiner

Macroscopic observation of circular defects

Knee-joint defect site (circular bone defects) (2 mm in diameter, 4 mm in depth)

Control

Chicken foot extract hydrolysate administration group (50 mg/day)

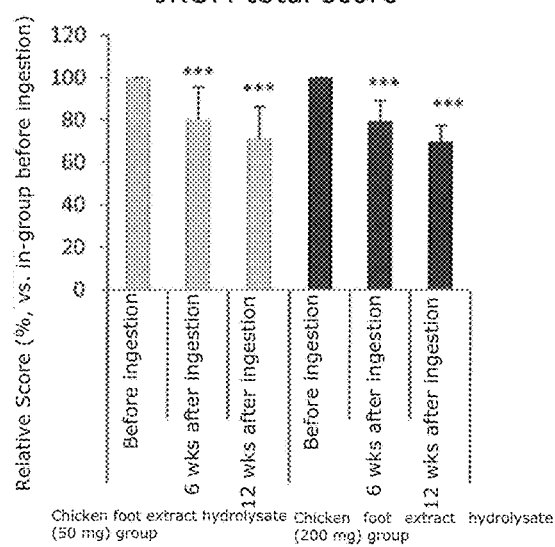
Fig. 12 JKOM total score
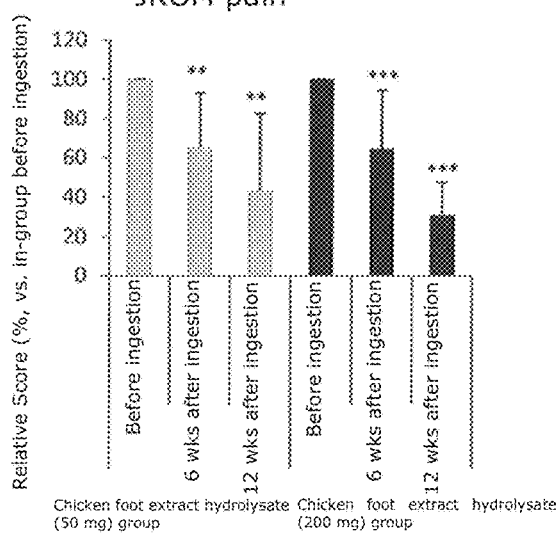
Fig. 13 JKOM pain
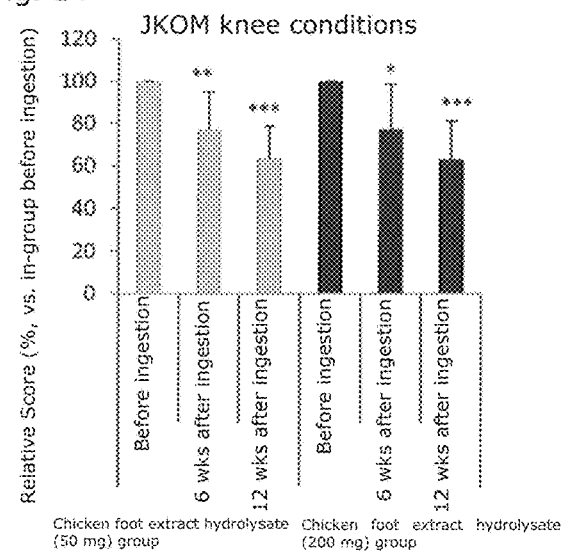
Fig. 14 JKOM knee conditions

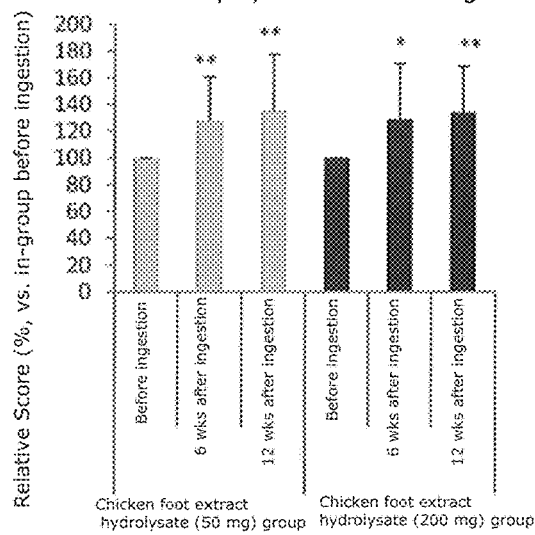
Fig. 15 SF-36 physical functioning
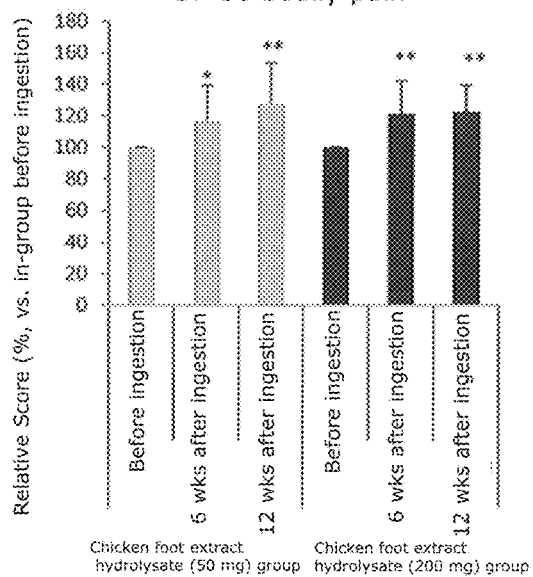
Fig. 16 SF-36 bodily pain
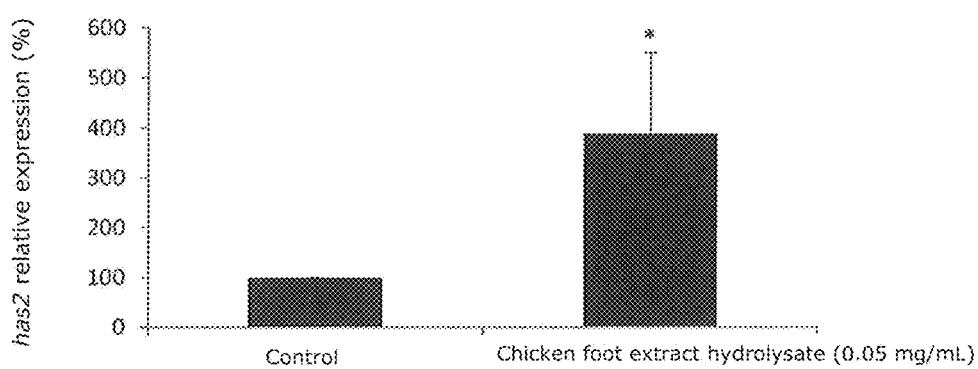
Fig. 17 Expression of hyaluronic acid synthase (*has2*) gene
t-test *p < 0.05

$p < 0.05$ vs. before application

HYALURONIC ACID PRODUCTION PROMOTING AGENT

CROSS REFERENCE TO RELATED APPLICATIONS

This application is a Continuation-In-Part of PCT International Application Number PCT/JP2015/084852, filed on Dec. 11, 2015, which designates the United States of America and was published in Japanese and, which is an International Application of and claims the benefit of priority to Japanese Patent Application No. 2015-023507, filed on Feb. 9, 2015. The disclosures of the above-referenced applications are hereby expressly incorporated by reference in their entireties.

TECHNICAL FIELD

The present invention relates to a hyaluronic acid production promoting agent. In particular, the present invention relates to a hyaluronic acid production promoting agent comprising poultry feet or a processed product thereof as an active ingredient.

BACKGROUND ART

For the prevention or treatment of various chondropathies, the growth of chondrogenic cells and the expression of their differentiation function are important. That is, the growth and maturation of chondrogenic cells are considered to promote normal growth of bones, facilitate repair of bone fracture, maintain smooth movement of joints, and restore decreased movement of joints. Several growth factors for chondrogenic cells have been reported, including transforming growth factor (TGF)-β1, insulin-like growth factor (IGF)-1, basic fibroblast growth factor (bFGF), PTH-related peptide (PTHrP), hepatocyte growth factor (HGF), and bone morphogenetic protein (BMP). However, clinical applications of chondrocyte growth-promoting drugs that are excellent in safety, stability and efficacy have not been established or practiced yet. Consequently, joint disorders remain a great burden on humans.

Knee osteoarthritis patients account for the largest proportion of joint disorder patients. One of the causes of knee osteoarthritis is aging, and the incidence of the disease is expected to increase in this aging society. The incidence rate is particularly higher in women than men, and the sex ratio of men to women patients is 1 to 4. Joint disorders in which the main lesion is degeneration of cartilage (e.g., joint diseases) have conventionally been prevented or treated mostly with symptomatic therapy by direct injection of hyaluronic acid into knee joints or by using antiinflammatories, or with drug therapy using bone resorption inhibitors such as estrogen and calcitonin, or aspirin, or nonsteroidal anti-inflammatory drugs (NSAIDs). However, these therapies are not effective enough, and the drugs are well-known to cause adverse effects such as digestive tract disorders. Under these circumstances, there has been a great demand for prophylactic or alleviating drugs that are highly effectively and safely used for treatment of joint injuries and joint disorders.

The inventors have found a beneficial action of an egg yolk hydrolysate on cartilage (Patent Literature 1). However, there has been no report on an action of poultry feet or a processed product thereof on cartilage.

CITATION LIST

Patent Literature

Patent Literature 1: WO 2014/007318

SUMMARY OF INVENTION

Technical Problem

An object of the present invention is to provide a novel hyaluronic acid production promoting agent that can be safely and effectively used for the prevention, alleviation or treatment of a joint disorder, or for the improvement of skin conditions, such as dryness, wrinkles, tension and moisture.

Solution to Problem

The present invention was made to solve the above problems and includes the following.
(1) A hyaluronic acid production promoting agent comprising poultry feet or a processed product thereof.
(2) The agent according to the above (1), which is for the prevention or treatment of a joint disorder.
(3) The agent according to the above (1) or (2), which is for the alleviation of knee pain or bodily pain or the improvement of physical functioning.
(4) The agent according to the above (1), which is for the improvement of skin dryness, wrinkles or skin tension or the moisturization of the skin.
(5) The agent according to any of the above (1) to (4), further comprising N-acetylglucosamine, glucosamine, or a pharmacologically acceptable salt thereof.
(6) The agent according to any of the above (1) to (5), wherein the processed product of poultry feet is a hydrolysate of an extract of poultry feet.
(7) The agent according to the above (6), wherein the poultry feet to be subjected to extraction are crushed or minced poultry feet.
(8) The agent according to the above (6) or (7), wherein the hydrolysate of the extract, when subjected to gel filtration chromatography, shows peaks with molecular weights ranging from 500 to 30000 Da and the area of the peaks accounts for 60% or more of the total peak area.
(9) The agent according to any of the above (1) to (8), which has a promoting effect on hyaluronic acid production, on the expression of a hyaluronic acid synthase gene, or on cartilage formation.
(10) A health food, a food additive, or a dietary supplement, comprising the agent according to any of the above (1) to (9).
(11) The health food, the food additive or the dietary supplement according to the above (10), further comprising a pharmaceutical excipient.
(12) The health food, the food additive or the dietary supplement according to the above (11), wherein the pharmaceutical excipient is in the form of a liquid or solid.
(13) The health food, the food additive or the dietary supplement according to any of the above (10) to (12), which is in the form of a tablet or a drink.
(14) A medicament comprising the agent according to any of the above (1) to (9).
(15) The medicament according to the above (14), which is for the prevention or treatment of a joint disorder.
(16) A cosmetic product or a quasi-drug, comprising the agent according to any of the above (1) to (9).

(17) A method for promoting hyaluronic acid production, the method comprising administering an effective amount of the agent according to any of the above (1) to (9) to a mammal.
(18) The agent according to any of the above (1) to (9) for use in promoting hyaluronic acid production.
(19) Use of the agent according to any of the above (1) to (9) for the production of an agent for promoting hyaluronic acid production.
(20) Use of the agent according to any of the above (1) to (9) for the promotion of hyaluronic acid production.
(21) A method for promoting hyaluronic acid production, the method comprising administering an effective amount of a hyaluronic acid production promoting agent comprising poultry feet or a processed product thereof to a mammal.
(22) The method according to the above (21), which is for the prevention or treatment of a joint disorder.
(23) The method according to the above (21), which is for the alleviation of knee pain or bodily pain or the improvement of physical functioning.
(24) The method according to the above (21), which is for the improvement of skin dryness, wrinkles or skin tension or the moisturization of the skin.
(25) The method according to the above (21), wherein the hyaluronic acid production promoting agent further comprises N-acetylglucosamine, glucosamine, or a pharmacologically acceptable salt thereof.
(26) The method according to the above (21), wherein the processed product of poultry feet is a hydrolysate of an extract of poultry feet.
(27) The method according to the above (26), wherein the poultry feet to be subjected to extraction are crushed or minced poultry feet.
(28) The method according to the above (26), wherein the hydrolysate of the extract, when subjected to gel filtration chromatography, shows peaks with molecular weights ranging from 500 to 30000 Da and the area of the peaks accounts for 60% or more of the total peak area.
(29) The method according to the above (21), which is for the promotion of expression of a hyaluronic acid synthase gene or the promotion of cartilage formation.
(30) The method for promoting hyaluronic acid production according to the above (21), wherein the processed product of poultry feet is a peptide of 100 amino acid residues or less containing the amino acid sequence phenylalanine-hydroxyproline and an additional amino acid sequence and having a promoting effect on hyaluronic acid production, a derivative thereof, or a salt thereof.
(31) The method according to the above (21), wherein the processed product of poultry feet is a phenylalanine-hydroxyproline dipeptide, a derivative thereof, or a salt thereof.
(32) A method for promoting hyaluronic acid production, the method comprising administering, to a mammal, an effective amount of a peptide of 100 amino acid residues or less containing the amino acid sequence phenylalanine-hydroxyproline and an additional amino acid sequence and having a promoting effect on hyaluronic acid production, a derivative thereof, or a salt thereof.
(33) A method for promoting hyaluronic acid production, the method comprising administering an effective amount of a phenylalanine-hydroxyproline dipeptide, a derivative thereof, or a salt thereof to a mammal.

Advantageous Effects of Invention

The present invention provides a hyaluronic acid production promoting agent. Poultry feet or a processed product thereof containing an active ingredient is a safe, natural material from poultry that has a long history as food, and can therefore be widely used in daily consumable products, such as food and drink products, medicaments, animal feeds, etc. The hyaluronic acid production promoting agent of the present invention improves skin dryness, wrinkles or skin tension. The hyaluronic acid production promoting agent of the present invention can also be used as a skin moisturizing agent. The hyaluronic acid production promoting agent of the present invention has effects of alleviating knee pain, knee conditions and bodily pain and improving physical functioning, etc., and can therefore be used as a prophylactic or therapeutic agent for a joint disorder. The hyaluronic acid production promoting agent of the present invention effectively improves the quality of life (QOL) of a subject suffering from knee pain. The hyaluronic acid production promoting agent of the present invention is particularly effective for women.

BRIEF DESCRIPTION OF DRAWINGS

FIG. 12 shows the total score of JKOM assessment.
FIG. 13 shows the pain score of JKOM assessment.
FIG. 14 shows the knee condition score of JKOM assessment.
FIG. 15 shows the physical functioning score of SF-36 assessment.
FIG. 16 shows the bodily pain score of SF-36 assessment.
FIG. 17 is a graph showing that a chicken foot extract hydrolysate promotes the expression of a hyaluronic acid synthase gene in human dermal fibroblasts.

DESCRIPTION OF EMBODIMENTS

Figure 1:
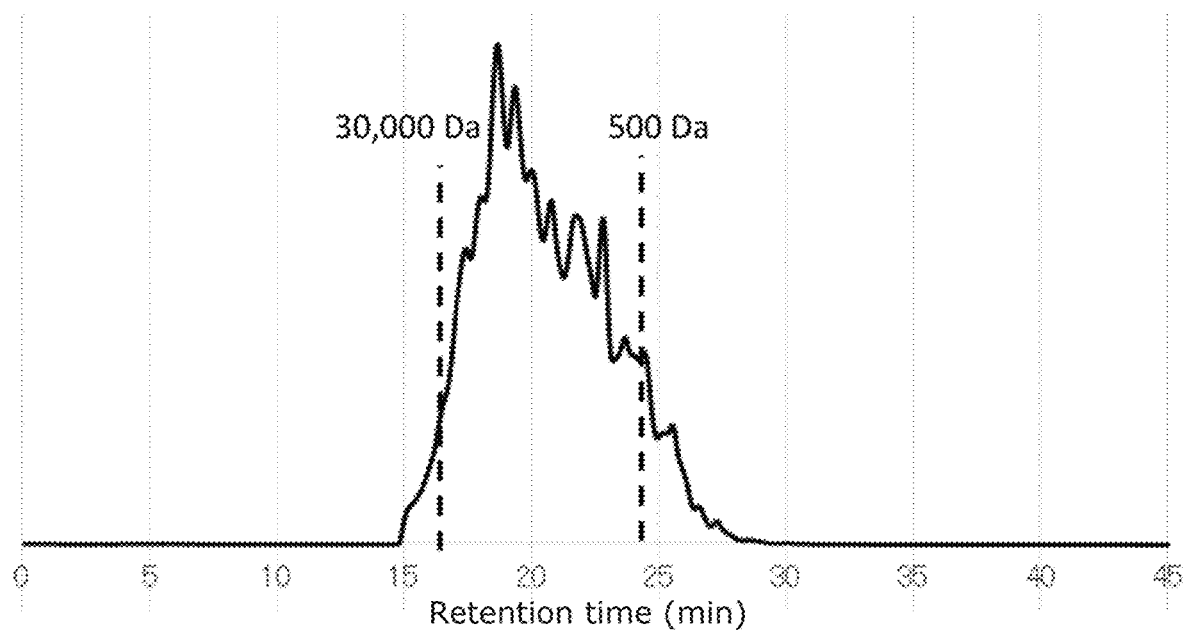
FIG. 1 shows the molecular weight distribution of a hydrolysate of a chicken foot extract (hereinafter simply called a chicken foot extract hydrolysate).

The present invention provides a hyaluronic acid production promoting agent comprising poultry feet or a processed product thereof as an active ingredient (hereinafter also called an agent of the present invention). The amount of the poultry feet or a processed product thereof contained in the agent of the present invention may be 0.01 to 100% by mass, 0.1 to 50% by mass, or 0.1 to 10% by mass.

Poultry Feet

Poultry feet are not commonly eaten by people. Poultry feet are usually disposed as waste, and are therefore usually not commercially distributed as food. Examples of the poultry include chickens, ducks, emus, geese, Indian peafowls, mute swans, ostriches, turkeys, guinea fowls, ring-necked pheasants, golden pheasants, rheas, quails, etc. Particularly preferred are chickens. A preferred chicken is Mitsuse chicken. Mitsuse chicken is a breed derived from French red chickens, and raised mainly in mountainous regions in the northern Kyushu, such as Saga, Fukuoka, Nagasaki and Oita prefectures.

Poultry feet are body parts under the belly and thigh, or a part thereof. The feet may include the belly and thigh, but preferably do not include the belly or thigh. The feet may include bones, spurs, toes, and leg feathers.

Poultry feet may be in a raw state, or a boiled, roasted or dried state. Crushing of the feet is performed by a known method. Crushing may be performed using an instrument, such as a mixer and a mill.

Processed Product of Poultry Feet

The poultry feet may be pre-treated before processed into a processed product. The pre-treatment may be, for example, pH treatment, removal of impurities, etc. The pH treatment may be performed by immersing the poultry feet in, for example, an acidic liquid, an alkaline liquid, a neutral liquid, or the like. The temperature of the liquid for immersion may be, for example, room temperature (5 to 35° C.), 0 to 5° C., or 35 to 50° C., but is preferably room temperature (5 to 35° C.). The duration of the immersion may be, for example, 1 hour to 1 week, or 3 to 18 hours, but is preferably 6 hours to 4 days, more preferably 1 to 3 days. The pH of the liquid can be adjusted by, for example, adding a strong acid (e.g., hydrochloric acid), a strong alkali (sodium hydroxide), or the like to the liquid containing the poultry feet. The pH of the acidic liquid for immersion may be 0 to 6, but is preferably 4 to 6. The pH of the neutral liquid for immersion may be 6 to 8. The pH of the alkaline liquid for immersion may be 8 to 14, but is preferably 8 to 10. In cases where the poultry feet are pre-treated in the acidic liquid or the alkaline liquid, the liquid may later be neutralized with an alkaline liquid or an acidic liquid. The ratio of the poultry feet (kg) to the immersion liquid (L) in the pH treatment is preferably 0.1 to 1 kg per liter, and is more preferably 0.4 to 0.6 kg per liter. The removal of impurities may be performed by filtration etc. Filtration may be performed by a known method.

A processed product of the poultry feet may be a processed product of crushed or minced poultry feet. The crushed or minced poultry feet are not limited to a particular type, and may be prepared by a known method. The processed product of the poultry feet is also not limited to a particular type, but is particularly preferably, for example, a product obtainable by treating the poultry feet or the feet in a crushed state by extraction, decomposition, drying, and/or the like. The processed product of the poultry feet is preferably a hydrolysate of an extract of the poultry feet or the feet in a crushed state, and is more preferably a dried product of a hydrolysate of an extract of the poultry feet or the feet in a crushed state. The hydrolysate or the dried product is a peptide-containing mixture. The extraction may be performed in, for example, water with a neutral pH. The extraction solvent may be a hydrophilic solvent other than water, and examples of such an extraction solvent include ethanol, acetone, tetrahydrofuran, butanol, propanol, and a mixture thereof. Particularly preferred is a mixture of such a hydrophilic solvent and water. The extraction temperature may be 5 to 100° C., 50 to 97° C., 70 to 95° C., or 80 to 90° C. The extraction time may be 1 hour to 1 week, 1 to 24 hours, 1 to 12 hours, or 5 to 7 hours. Extraction at the above extraction temperature for the above extraction time will efficiently yield proteins, peptides, and the like that have a promoting effect on hyaluronic acid production. Crushed poultry feet are preferably prepared by crushing the feet with a crushing machine. Examples of the crushing machine include Waring blenders, mill mixers, homogenizers, single shaft shredders with a pusher, high-speed single shaft crushers, medium-speed single shaft crushers, low-speed single shaft shredders, double shaft shredders, four shaft shredders, hammer mills, disc mills, press machines, etc. The size of the crushed poultry feet may be, for example, 0.5 to 3 cm square, but is preferably 0.5 to 1 cm square. After extraction, the extract is obtained by, for example, removing the extraction solvent from the liquid.

The extract is then usually subjected to hydrolysis. Hydrolysis may be enzymatic decomposition (using, for example, endoprotease, carboxypeptidase, collagenase, lipase, etc.) or chemical decomposition (using, for example, an acid or alkali etc.), but preferred is enzymatic decomposition. The enzyme may be a hydrolytic enzyme. Hydrolysis is particularly preferably performed on the proteins extracted from poultry feet or the feet in a crushed state. The enzyme used for protein hydrolysis is not particularly limited, but preferred is an enzyme that has protease or carboxypeptidase activity and is usable for food production. Examples of the enzyme include pepsin (EC.3.4.23.1), trypsin (EC.3.4.21.4), renin (EC.3.4.23.15), rennet, which contains renin and is used for cheese making, carboxypeptidase A (EC.3.4.17.1), proteases from *Bacillus* bacteria (trade name "Alcalase" produced by Novozymes A/S, trade name "Orientase 22BF" produced by HBI Enzymes Inc., trade name "Nukureishin" produced by HBI Enzymes Inc., trade name "Protease S 'Amano' G" produced by Amano Enzyme, Inc., trade name "THERMOASE PC10" produced by Daiwa Fine Chemicals Co., Ltd., etc.), proteases from *Aspergillus* fungi (trade name "Orientase ONS" produced by HBI Enzymes Inc., trade name "Orientase 20A" produced by HBI Enzymes Inc., trade name "Protease P 'Amano' 3G" produced by Amano Enzyme, Inc., trade name "Flavourzyme" produced by Novozymes A/S, etc.), etc. These proteolytic enzymes may be used alone or in combination of two or more types. Preferred are proteases from *Aspergillus* fungi, pepsin, and a combination thereof. The hydrolysis is preferably performed in an appropriate solvent, such as water.

The amount of the enzyme is appropriately adjusted depending on the conditions of the poultry feet and the enzyme to be used. For example, when 1 kg of a chicken feet extract is used as the raw material, the amount of the enzyme used is preferably 100 to 100000 units, and is more preferably 1000 to 30000 units. The enzymatic reaction temperature and the reaction time also vary depending on the conditions of the poultry feet and the enzyme to be used. Preferably, the hydrolysis is performed at about 25 to 75° C. for about 1 to 24 hours.

The thus prepared hydrolysate may be desalted if desired and directly used. Alternatively, the hydrolysate may be used after purification and/or fractionation by ultrafiltration, gel filtration, various column chromatographic techniques, membrane filter filtration, methods utilizing an isoelectric point, etc. A fraction containing a peptide or protein of interest is preferably dried to give the agent of the present invention.

The drying method may be concentration and drying; spray drying; lyophilization; or the like. The poultry feet or the feet in a crushed state, an extract thereof, or a hydrolysate thereof can be dried by a known method. The hydrolysate of extracted proteins from the poultry feet or the feet in a crushed state is preferably subjected to drying.

Preferably, the hydrolysate of the extract of the poultry feet or the feet in a crushed state, or the dried product of the hydrolysate, when subjected to gel filtration chromatography, shows peaks with molecular weights ranging from 500 to 30000 Da and the area of the peaks accounts for 60% or more of the total peak area. Preferably, the poultry feet or a processed product thereof, when subjected to gel filtration chromatography, shows peaks with molecular weights ranging from 500 to 30000 Da and the area of the peaks accounts for 70% or more of the total peak area. Preferably, the poultry feet or a processed product thereof, when subjected to gel filtration chromatography, shows peaks with molecular weights ranging from 500 to 30000 Da and the area of the peaks accounts for 75% or more of the total peak area. Preferably, the poultry feet or a processed product thereof, when subjected to gel filtration chromatography, shows peaks with molecular weights ranging from 500 to 30000 Da and the area of the peaks accounts for 80% or more of the total peak area.

The conditions of the gel filtration chromatography analysis may be as follows.

Column: YMC-pack Diol 60 (trade name) (6×300 mm) (YMC Co., Ltd.)
Eluent: 0.2 M potassium phosphate buffer with 0.2 M NaCl (pH 6.9)/acetonitrile (70:30 v/v)
Flow rate: 0.7 mL/min
Detection wavelength: 280 nm The processed product of the poultry feet is preferably a peptide of 100 amino acid residues or less containing the amino acid sequence phenylalanine-hydroxyproline and an additional amino acid sequence and having a promoting effect on hyaluronic acid production, a derivative thereof, or a salt thereof.

The processed product of the poultry feet is particularly preferably a peptide consisting of the amino acid sequence phenylalanine-hydroxyproline (hereinafter also called a Phe-Hyp dipeptide or a phenylalanine-hydroxyproline dipeptide), a derivative thereof, or a salt thereof.

The hydroxyproline herein may be 3-hydroxyproline or 4-hydroxyproline, but is preferably 4-hydroxyproline.

The amount of the "peptide of 100 amino acid residues or less containing the amino acid sequence phenylalanine-hydroxyproline and an additional amino acid sequence and having a promoting effect on hyaluronic acid production, a derivative thereof, or a salt thereof", the Phe-Hyp dipeptide, a derivative thereof, or a salt thereof contained in the hyaluronic acid production promoting agent is preferably 0.01 to 100% by mass, 1 to 100% by mass, 5 to 100% by mass, 10 to 100% by mass, 20 to 100% by mass, 30 to 100% by mass, 40 to 100% by mass, 50 to 100% by mass, 60 to 100% by mass, 70 to 100% by mass, 80 to 100% by mass, or 90 to 100% by mass. The hyaluronic acid production promoting agent may further comprise a pharmaceutical excipient. Preferred examples of the excipient include lactose hydrate, starch, crystalline cellulose, mannitol, anhydrous dibasic calcium phosphate, sucrose, etc. The pharmaceutical excipient may be in the form of a liquid or solid. The amount of the pharmaceutical excipient contained in the hyaluronic acid production promoting agent may be 0.01 to 50% by mass or 0.01 to 10% by mass.

The present disclosure also includes a method for promoting hyaluronic acid production, the method comprising administering, to a mammal, an effective amount of the peptide of 100 amino acid residues or less containing the amino acid sequence phenylalanine-hydroxyproline and an additional amino acid sequence and having a promoting effect on hyaluronic acid production, a derivative thereof, or a salt thereof.

The present disclosure also includes a method for promoting hyaluronic acid production, the method comprising administering an effective amount of the Phe-Hyp dipeptide, a derivative thereof, or a salt thereof to a mammal.

The present disclosure also includes a method for promoting hyaluronic acid production, the method comprising administering, to a mammal, a composition comprising 50 to 99.99% by mass, preferably 90 to 99.99% by mass, of the peptide of 100 amino acid residues or less containing the amino acid sequence phenylalanine-hydroxyproline and an additional amino acid sequence and having a promoting effect on hyaluronic acid production, a derivative thereof, or a salt thereof. The composition may further comprise a pharmaceutical excipient. The pharmaceutical excipient includes those described above, and preferred examples of the excipient include lactose hydrate, starch, crystalline cellulose, mannitol, anhydrous dibasic calcium phosphate, sucrose, etc. The pharmaceutical excipient may be in the form of a liquid or solid. The amount of the pharmaceutical excipient contained in the composition may be 0.01 to 50% by mass or 0.01 to 10% by mass.

The "peptide of 100 amino acid residues or less containing the amino acid sequence phenylalanine-hydroxyproline and an additional amino acid sequence and having a promoting effect on hyaluronic acid production, a derivative thereof, or a salt thereof", or the "Phe-Hyp dipeptide, a derivative thereof, or a salt thereof" may be contained in, for example, the poultry feet or a hydrolysate thereof. Alternatively, the peptide, the Phe-Hyp dipeptide, a derivative thereof, or a salt thereof may be contained in a hydrolysate obtainable by hydrolysis, e.g., enzymatic hydrolysis, of an extract extracted from crushed poultry feet using an extraction solvent such as water. The peptide of interest, a derivative thereof, or a salt thereof may be purified by ultrafiltration or various chromatographic techniques, such as HPLC.

In another embodiment, the "peptide of 100 amino acid residues or less containing the amino acid sequence phenylalanine-hydroxyproline and an additional amino acid sequence and having a promoting effect on hyaluronic acid production, a derivative thereof, or a salt thereof", or the "Phe-Hyp dipeptide, a derivative thereof, or a salt thereof" can easily be produced by solid-phase synthesis (the Fmoc or Boc method) or liquid-phase synthesis following the usual peptide synthesis protocol known in the art.

Hereinafter, the "peptide of 100 amino acid residues or less containing the amino acid sequence phenylalanine-hydroxyproline and an additional amino acid sequence and having a promoting effect on hyaluronic acid production" is also referred to as the "peptide α".

Use of the peptide α, a derivative thereof, or a salt thereof is preferred, and use of the Phe-Hyp dipeptide, a derivative thereof, or a salt thereof is more preferred, due to the following advantages: the peptides, a derivative thereof, or a salt thereof can promote cartilage matrix production by chondrogenic cells; the peptides, a derivative thereof, or a salt thereof can enhance the expression of cartilage differentiation-related genes, such as SOX9 (Sry-type human mobility group box 9), Acan (aggrecan), Col X (type X collagen) and the has2 gene; the peptides, a derivative thereof, or a salt thereof can promote hyaluronic acid production in knee joints; and/or the peptides, a derivative thereof, or a salt thereof can prevent or treat a joint disorder; or the effects of the present invention can be better exhibited by the peptides, a derivative thereof, or a salt thereof.

The total number of amino acid residues in the peptide α, a derivative thereof, or a salt thereof is not particularly limited, but is preferably 100 or less, more preferably 50 or less, further preferably 20 or less, further preferably 10 or less, further preferably 8 or less, further preferably 5 or less, further preferably 4 or less, or further preferably 3 or less.

When the total number of amino acid residues is 3, the peptide α is preferably the tripeptide "glycine-phenylalanine-hydroxyproline", or the tripeptide "phenylalanine-hydroxyproline-glycine". The effects of the present invention can be better exhibited by these tripeptides.

When the total number of amino acid residues is 4 or more, the peptide α preferably contains one or more amino acid sequences selected from the group consisting of the amino acid sequences Phe-Hyp, Gly-Phe-Hyp, and Phe-Hyp-Gly. In these cases where the peptide α contains one or more of these amino acid sequences, the amino acid sequence(s) may be located at the C-terminus, N-terminus or in the middle of the peptide α. The effects of the present invention can be better exhibited by such a peptide α.

The C-terminus of a derivative of the peptide α or of the Phe-Hyp dipeptide, the peptides each being represented by a particular amino acid sequence, may be a carboxyl group (—COOH), a carboxylate (—COO$^-$), an amide (—CONH$_2$) or an ester (—COOR). Examples of R of the ester include $C_{1-6}$ alkyl groups, such as methyl, ethyl, n-propyl, isopropyl and n-butyl; $C_{3-8}$ cycloalkyl groups, such as cyclopentyl and cyclohexyl; $C_{6-12}$ aryl groups, such as phenyl and α-naphthyl; $C_{7-14}$ aralkyl groups including phenyl-$C_{1-2}$ alkyl groups, such as benzyl and phenethyl, and α-naphthyl-$C_{1-2}$ alkyl groups, such as α-naphthylmethyl; and a pivaloyloxymethyl group, which is commonly used as an ester for oral administration. Examples of the amide include an amide; an amide substituted with one or two $C_{1-6}$ alkyl groups; an amide substituted with one or two $C_{1-6}$ alkyl groups substituted with a phenyl group; and an amide that forms a 5- to 7-membered azacycloalkane containing the nitrogen atom of the amide group.

When the derivative of the peptide α has a carboxyl group or a carboxylate at a position other than the C-terminus, the derivative of the peptide α also includes derivatives with amidated or esterified carboxyl or carboxylate.

The derivative of the peptide α or of the Phe-Hyp dipeptide also includes derivatives in which the N-terminal amino group is protected with a protecting group (e.g., a $C_{1-6}$ acyl group including a formyl group and $C_{2-6}$ alkanoyl groups such as acetyl), derivatives in which a N-terminal glutamyl group generated by in vivo cleavage of the N-terminus is converted to a pyroglutamate, and derivatives in which a substituent (e.g., —OH, —SH, an amino group, an imidazole group, an indole group, or a guanidino group) on an amino acid side chain in the molecule is protected with a suitable protecting group (e.g., a $C_{1-6}$ acyl group including a formyl group and $C_{2-6}$ alkanoyl groups such as acetyl).

The side chains of the amino acids constituting the derivative of the peptide α or of the Phe-Hyp dipeptide may be modified with a substituent. Examples of the substituent include, but are not limited to, a fluorine atom, a chlorine atom, a bromine atom, a cyano group, a carboxyl group, a hydroxy group, a nitro group, an alkyl group, a cycloalkyl group, an alkoxy group, an amino group, and a phosphate group. The side-chain substituent may be protected with a protecting group. The derivative also includes glycopeptides, which are peptides having sugar chains.

The derivative of the peptide α or of the Phe-Hyp dipeptide may form a salt. The salt is preferably physiologically acceptable. Examples of the physiologically acceptable salt include salts with an inorganic or organic acid, such as hydrochloric acid, sulfuric acid, phosphoric acid, lactic acid, tartaric acid, maleic acid, fumaric acid, oxalic acid, malic acid, citric acid, oleic acid, and palmitic acid; salts with a hydroxide or a carbonate of an alkali metal, such as sodium, potassium and calcium, salts with a hydroxide or a carbonate of an alkaline earth metal, and salts with aluminum hydroxide or carbonate; and salts with an organic base, such as triethylamine, benzylamine, diethanolamine, t-butylamine, dicyclohexylamine, and arginine.

The derivative of the peptide α or of the Phe-Hyp dipeptide may contain a D-amino acid or a non-naturally occurring amino acid to the extent that the derivative retains the characteristics of the original peptide. The peptides of the present invention or a derivative thereof may contain another substance linked thereto to the extent that the peptides or the derivative retains the characteristics of the original peptide. Examples of the substance linkable to the peptides or a derivative thereof include other peptides, lipids, sugars, sugar chains, an acetyl group, and naturally occurring or synthetic polymers. The peptide α may be subjected to modification such as glycosylation, side-chain oxidation, and phosphorylation to the extent that the resulting modified peptide retains the characteristics of the original peptide.

Hyaluronic Acid Production Promoting Agent

Poultry feet or a processed product thereof has a promoting effect on hyaluronic acid production etc., and can serve as a suitable active ingredient of an agent for improving skin dryness, wrinkles or skin tension, for moisturizing the skin, for preventing or treating a joint disorder, or for other purposes. The prophylactic or therapeutic agent for a joint disorder exhibits effects of alleviating knee pain, knee conditions and bodily pain and improving physical functioning, etc. The term "joint disorder" is interchangeable with the term "cartilage disorder". Examples of the joint disorder include osteoarthritis, cartilage defects, cartilage injury, and meniscus injury. The agent of the present invention has a promoting effect on hyaluronic acid production, on the expression of hyaluronic acid synthase genes, such as the HAS1 gene, the HAS2 gene and the HAS3 gene, on cartilage formation, etc. The "agent of the present invention"

has a function of "promoting hyaluronic acid production", a function of "promoting the expression of a hyaluronic acid synthase gene", a function of "promoting cartilage formation", etc. Whether a sample has a promoting effect on hyaluronic acid production can be determined by, for example, the method described in Test Example 1. For example, if hyaluronic acid production is greater in the presence of the sample than in a control in the absence of the sample, the sample is determined to have a promoting effect on hyaluronic acid production. Whether a sample has a promoting effect on the expression of a hyaluronic acid synthase gene can be determined by, for example, the method described in Test Example 2. For example, if the expression of a hyaluronic acid synthase gene is greater in the presence of the sample than in a control in the absence of the sample, the sample is determined to have a promoting effect on the expression of the hyaluronic acid synthase gene. Whether a sample has a promoting effect on cartilage formation can be determined by, for example, the method described in Test Example 3. For example, if the Alcian blue- or Safranin O-stained area of cartilage in an osteochondral defect animal model with administration of the sample is significantly different from that in the animal model without administration of the sample, the sample is determined to have a promoting effect on cartilage formation. Whether a sample has effects of alleviating knee pain, knee conditions and bodily pain and improving physical functioning, etc. can be determined by, for example, the method described in Test Example 4. For example, if an assessment score measured by WOMAC (Western Ontario and McMaster Universities Osteoarthritis Index) assessment, SF-36 (MOS 36-Item Short-Form Health Survey), JKOM (Japanese Knee Osteoarthritis Measure) assessment, etc. after administration of the sample is significantly different from that before administration of the sample, the sample is determined to have effects of alleviating knee pain, knee conditions and bodily pain and improving physical functioning, etc. Whether a sample has an effect of improving skin dryness, wrinkles or skin tension can be determined by, for example, the method described in Test Example 5 (2). For example, if an assessment score measured by VAS for "skin dryness", "skin tension", "fine lines at the outer corner of the eyes", etc. after administration of the sample is significantly different from that before administration of the sample, the sample is determined to have an effect of improving the skin conditions.

The amount of the poultry feet or a processed product thereof contained in the agent of the present invention is not particularly limited, but is preferably about 0.05 to about 50% by mass, more preferably about 0.1 to about 25% by mass. The daily dose of the poultry feet or a processed product thereof varies depending on the subject, but in cases where the subject is, for example, an adult human, the daily dose of the poultry feet or a processed product thereof, preferably a hydrolysate of an extract of chicken feet, is typically about 0.05 to about 2000 mg/day, and is preferably about 0.1 to about 1000 mg/day.

The daily dose of the "peptide of 100 amino acid residues or less containing the amino acid sequence phenylalanine-hydroxyproline and an additional amino acid sequence and having a promoting effect on hyaluronic acid production, a derivative thereof, or a salt thereof", or the "Phe-Hyp dipeptide, a derivative thereof, or a salt thereof" is, for example, when the subject is an adult human, typically about 0.05 to about 2000 mg/day, preferably about 0.1 to about 1000 mg/day.

Medicament

The present invention provides a medicament having a promoting effect on hyaluronic acid production. The medicament of the present invention may be any type of medicament as long as it comprises the poultry feet or a processed product thereof. The medicament of the present invention can be administered to a mammal via an oral or parenteral route. Examples of oral preparations include granules, powders, tablets (including sugar-coated tablets), pills, capsules, syrups, emulsions, suspensions, etc. Examples of parenteral preparations include injections (e.g., subcutaneous, intravenous, intramuscular, and intraperitoneal injections), intravenous infusions, external preparations (e.g., transnasal preparations, transdermal preparations, and ointments), suppositories (e.g., rectal suppositories, and vaginal suppositories), etc. These preparations can be produced using a pharmaceutically acceptable carrier in accordance with the usual practice in the field. Examples of the pharmaceutically acceptable carrier include excipients, binders, diluents, additives, fragrances, buffering agents, thickeners, colorants, stabilizers, emulsifiers, dispersants, suspending agents, preservatives, etc. Specific examples of the carrier include magnesium carbonate, magnesium stearate, talc, sugar, lactose, pectin, dextrin, starch, gelatin, tragacanth, methylcellulose, sodium carboxymethyl cellulose, low melting wax, cacao butter, etc.

The oral solid preparations (tablets, pills, capsules, powders, granules, etc.) can be produced by mixing the active ingredient with, for example, an excipient (lactose, mannitol, glucose, microcrystalline cellulose, starch, etc.), a binder (hydroxypropyl cellulose, polyvinylpyrrolidone, magnesium aluminometasilicate, etc.), a disintegrant (calcium carboxymethyl cellulose etc.), a lubricant (magnesium stearate etc.), a stabilizer, a solubilizer (glutamic acid, aspartic acid, etc.) and/or the like, and processing the mixture into the desired dosage form in the usual manner. If needed, the oral solid preparations may be covered with a coating material (sucrose, gelatin, hydroxypropyl cellulose, hydroxypropyl methylcellulose phthalate, etc.), or the oral solid preparations may be covered with two or more coating layers.

The oral liquid preparations (solutions, suspensions, emulsions, syrups, elixirs, etc.) can be produced by dissolving, suspending or emulsifying the active ingredient in a commonly used diluent (purified water, ethanol, a mixture of them, etc.). The oral liquid preparations may further contain a wetting agent, a suspending agent, an emulsifier, a sweetener, a flavoring agent, a fragrance, a preservative, a buffering agent and/or the like.

The injections include solutions, suspensions, emulsions, and solid injectable preparations that are intended to be dissolved or suspended in a solvent at the time of use. The injections can be produced by dissolving, suspending or emulsifying the active ingredient in a solvent. Examples of the solvent include distilled water for injection, physiological saline, vegetable oils, alcohols such as propylene glycol, polyethylene glycol and ethanol, and a combination thereof. The injections may further contain a stabilizer, a solubilizer (glutamic acid, aspartic acid, polysorbate 80 (registered trademark), etc.), a suspending agent, an emulsifier, a soothing agent, a buffering agent, a preservative, and/or the like. The injections are sterilized in the final step of the production process or produced in an aseptic manner. Alternatively, sterile solid preparations, for example, lyophilized preparations may be produced for use as injections. Such sterile solid preparations are intended to be dissolved in a sterilized or aseptic distilled water for injection or another solvent at the time of use.

Dietary Supplement

The present invention provides a dietary supplement comprising the agent of the present invention. The dietary supplement of the present invention may be any type of dietary supplement as long as it comprises the poultry feet or a processed product thereof. The dietary supplement of the present invention may be in the form of an oral solid preparation (a tablet, a pill, a capsule, a powder, granules, etc.), an oral liquid preparation (a drink), or the like. These preparations can be produced in the same manner as in the production of the medicament. The dietary supplement of the present invention preferably further comprises a pharmaceutical excipient. The pharmaceutical excipient includes those described above, and preferred examples of the excipient include lactose hydrate, starch, crystalline cellulose, mannitol, anhydrous dibasic calcium phosphate, sucrose, etc. The pharmaceutical excipient may be in the form of a liquid or solid.

Health Food

The present invention provides a health food comprising the agent of the present invention. The health food of the present invention may be any type of health food as long as it comprises the poultry feet or a processed product thereof. The health food of the present invention may be in the form of an oral solid preparation (a tablet, a pill, a capsule, a powder, granules, etc.), an oral liquid preparation (a drink), or the like, and is preferably in the form of a tablet, a drink, or the like. The health food of the present invention include functional foods, foods with functional claims, foods with nutrient function claims, foods for specified health use, and foods for sick people. The form of the health food is not particularly limited, and examples thereof include drinks such as tea drink, soft drink (beverage), carbonated drink, nutritional drink, fruit juice and lactic drink; noodles such as buckwheat noodle, wheat noodle, Chinese noodle and instant noodle; sweets and bakery such as hard candy, candy, chewing gum, chocolate, snack, biscuit, jelly, jam, cream, baked sweets and bread; processed fishery and livestock products such as fish cake, ham and sausage; dairy products such as yogurt, processed milk and fermented milk (cheese); fats, oils and processed fat and oil products such as vegetable oil, tempura oil, margarine, mayonnaise, shortening, whipped cream and dressing; seasonings such as sauce and dipping sauce; retort pouch food products such as curry, stew, rice bowl, rice porridge and rice soup; and frozen desserts such as ice cream, sherbet and shaved ice. The health food of the present invention preferably further comprises a pharmaceutical excipient. Examples of the excipient include lactose hydrate, starch, crystalline cellulose, mannitol, anhydrous dibasic calcium phosphate, sucrose, etc. The pharmaceutical excipient may be in the form of a liquid or solid. The health food of the present invention may be those distributed from a warehouse.

Food Additive

The present invention provides a food additive comprising the agent of the present invention. The food additive of the present invention may be any type of food additive as long as it comprises the poultry feet or a processed product thereof. The food additive of the present invention may be in the form of a solid preparation (a tablet, a pill, a capsule, a powder, granules, etc.), a liquid preparation (a drink), or the like. The form of the food additive of the present invention is not particularly limited, and may be, for example, a liquid, a paste, a powder, flakes, granules, etc. The food additive of the present invention also includes an additive for drinks. The food additive of the present invention can be produced in accordance with the conventional production method for food additives. The food additive of the present invention preferably further comprises a pharmaceutical excipient. Examples of the excipient include the excipients described above, for example, lactose hydrate, starch, crystalline cellulose, mannitol, anhydrous dibasic calcium phosphate, sucrose, etc. The pharmaceutical excipient may be in the form of a liquid or solid.

Cosmetic Product or Quasi-Drug

The present invention provides a cosmetic product or a quasi-drug comprising the agent of the present invention. The cosmetic product or the quasi-drug of the present invention may be any type of cosmetic product or quasi-drug as long as it comprises the poultry feet or a processed product thereof. The form of the cosmetic product or the quasi-drug is not particularly limited. Preferred examples of the form of the cosmetic product or the quasi-drug include external preparations for skin (facial toners, milky lotions, foundations, hand creams, essences, etc.), shampoos, conditioners, hair treatment agents, hair care agents, hair styling agents, face packs, soaps (including facial washes), body shampoos, hair growers, bath additives, and a solution. Depending on the purpose, the cosmetic product or the quasi-drug of the present invention may further contain an ingredient generally used in cosmetic products and quasi-drugs, if desired. Examples of such ingredient include stabilizers, surfactants, lubricants, buffering agents, sweeteners, flavor improvers, binders, antioxidants, coating agents, wetting agents, flavoring agents, flavors, colorants, sugar coating agents, isotonic agents, emulsifiers, thickeners, pH adjusting agents, excipients, dispersants, disintegrants, antiseptics, preservatives, solubilizers, solubilizing agents, oils, moisturizers, ultraviolet absorbers, fillers, sequestering agents, sunscreen agents, defoaming agents, softening agents, propellants, acidifying and basifying agents, silicones, vitamins, dyes, pigments, nanopigments, organic solvents (such as alcohol), water, etc. Preferred dosage forms include solid preparations, liquid preparations, lotions, emulsions, gels, creams, ointments, and aerosols, but the dosage form is not limited thereto as long as the dosage form is suitable for external use.

Animal Feed

The present invention provides an animal feed comprising the agent of the present invention. The animal feed of the present invention may be any type of animal feed as long as it comprises the poultry feet or a processed product thereof. The animal feed of the present invention may be in the form of a solid preparation (a tablet, a pill, a capsule, a powder, granules, etc.), a liquid preparation (a drink), or the like. Specific examples of the animal feed include animal feeds for domestic animals, such as cattle, horses, and pigs, animal feeds for poultry, such as chickens, and animal feeds for companion animals, such as dogs and cats. The animal feed of the present invention can be produced by adding the poultry feet or a processed product thereof to an animal feed. Alternatively, the animal feed of the present invention can be produced or processed by the conventional method for producing animal feeds. The animal feed of the present invention preferably further comprises a pharmaceutical excipient. Examples of the excipient include lactose hydrate, starch, crystalline cellulose, mannitol, anhydrous dibasic calcium phosphate, sucrose, etc. The pharmaceutical excipient may be in the form of a liquid or solid.

Combination with Other Ingredients

The poultry feet or a processed product is a multifunctional component and exhibits various effects. The poultry feet or a processed product is expected to exhibit a high additive or synergistic effect in combination with another active ingredient used for the promotion of hyaluronic acid production. Examples of another active ingredient for the treatment of chondropathies include egg yolk hydrolysates, glucosamine, chondroitin, type I collagen, type II collagen, N-acetylglucosamine, and a pharmacologically acceptable salt thereof. Particularly preferred are egg yolk hydrolysates, N-acetylglucosamine, glucosamine, a pharmacologically acceptable salt thereof, etc. Examples of the salt include a hydrochloric acid salt, a sulfuric acid salt, etc.

Therapeutic Method

The present invention also includes a method for promoting hyaluronic acid production, the method comprising administering an effective amount of the poultry feet or a processed product thereof to a mammal, including a human, in need of the promotion of chondrocyte formation. The present invention also provides a method for preventing or treating a joint disorder, a method for improving skin dryness, wrinkles or skin tension, and a method for moisturizing the skin, each method comprising administering an effective amount of the poultry feet or a processed product thereof to a mammal including a human. The present invention further includes a non-therapeutic method for preventing or alleviating a joint disorder, the method comprising orally administering the poultry feet or a processed product thereof to a human in need of the promotion of chondrocyte formation. The term "non-therapeutic" refers to a concept excluding medical practice, i.e., excluding therapeutic treatment of human or animal bodies.

The present invention also includes a method for promoting hyaluronic acid production, the method comprising administering an effective amount of the agent of the present invention to a mammal. Examples of the mammal include humans, non-human mammals (for example, rats, mice, rabbits, sheep, pigs, cattle, cats, dogs, monkeys, etc.). Preferred are humans, and particularly preferred are women. The route of administration is not particularly limited, and may be, for example, oral administration or transdermal administration (application to the skin).

Needless to say, the above-described techniques regarding the pharmaceutical preparations and the above-described embodiments of the therapeutic methods can also be applied to the "peptide of 100 amino acid residues or less containing the amino acid sequence phenylalanine-hydroxyproline and an additional amino acid sequence and having a promoting effect on hyaluronic acid production, a derivative thereof, or a salt thereof", or the "Phe-Hyp dipeptide, a derivative thereof, or a salt thereof".

Production Method

The present invention also includes a method for producing of the agent of the present invention. The production method of the present invention preferably comprises the step of crushing the poultry feet. The production method of the present invention preferably further comprises the steps of performing extraction from the obtained crushed poultry feet, decomposing the crushed poultry feet or the extract thereof, drying the crushed poultry feet, the extract thereof, or the decomposed product thereof, and formulating a composition using, as an active ingredient, the crushed poultry feet, the extract thereof, the decomposed product thereof, or the dried product thereof.

The present invention also includes the agent of the present invention for use in promoting hyaluronic acid production.

The present invention further includes use of the agent of the present invention for the production of a hyaluronic acid production promoting agent.

The present invention further includes use of the agent of the present invention for the promotion of hyaluronic acid production.

EXAMPLES

The present invention will be described in more detail below with reference to Examples, but the present invention is not limited thereto. The sign "%" means % by weight.

Production Example A: Production of Hydrolysate of Chicken Foot Extract (1) Preparation of Hydrolysate of Chicken Foot Extract Raw Mitsuse chicken feet were crushed into about 1 cm square pieces with a homogenizer. To 1 kg of the crushed chicken feet, 2 L of water was added, and hydrochloric acid was then added to adjust the pH to 4.0. After the mixture was stirred at room temperature for 2 days, the liquid for immersion was discarded and the chicken feet were washed with 2 L of water. To the washed chicken feet, 2 L of water was added, and the mixture was neutralized with sodium hydroxide. Extraction was performed at 90° C. for 6 hours. The resulting mixture was filtered to remove the solid matter to give a chicken foot extract liquid.

(2) Preparation of Hydrolysate of Chicken Foot Extract

To the chicken foot extract liquid obtained in the above (1), 10,000 units of an endoprotease was added, and the enzymatic reaction was allowed to proceed at 50° C. for 3 hours. The reaction mixture was heated at 90° C., and centrifuged at 3,000×g for 20 minutes to remove insoluble matter. After clarification by filtration, the filtrate was spray-dried by the conventional method to give about 110 g of a hydrolysate of the chicken foot extract.

The molecular weight analysis of the chicken foot extract hydrolysate was performed by gel filtration chromatography under the following conditions.

Column: YMC-pack Diol 60 (trade name) (6×300 mm) (YMC Co., Ltd.)
Eluent: 0.2 M potassium phosphate buffer with 0.2 M NaCl (pH 6.9)/acetonitrile (70:30)
Flow rate: 0.7 mL/min
Detection wavelength: 280 nm The results of the molecular weight analysis are shown in FIG. 1. As shown in FIG. 1, the chicken foot extract hydrolysate of Example 1 shows peaks with molecular weights ranging from 500 Da to 30,000 Da and the area of the peaks accounts for about 80% or more of the total peak area, which corresponds to the total amount of proteins, peptides and amino acids contained in the extract hydrolysate.

Test Example 1: Examination of Effect of Chicken Foot Extract Hydrolysate on Hyaluronic Acid Production by Chondrogenic Cells This study was performed using the mouse teratoma-derived chondrogenic culture cell line ATDC5 (RIKEN BANK, RBC0565), which is capable of differentiating into chondrocyte-like cells. ATDC5 cells were seeded in a 24-well plate at a density of $2 \times 10^4$ cells/mL per well and cultured in Eagle MEM medium containing 5% fetal calf serum (FCS) under 5% $CO_2$ at 37° C. After 3 days of culture, the cells were washed once with serum-free Eagle MEM medium. After addition of 1 mL of a test solution, the cells were cultured at 37° C. for 2 days. The test solution was previously prepared by dissolving a test sample in serum-free Eagle MEM medium and then sterilizing the solution by passing it through a 0.45-μm filter. The concentration of the test sample, i.e., the chicken foot extract hydrolysate etc., in the test solution was adjusted to a final concentration of 1 mg/mL in each well. At end of culture, the hyaluronic acid concentration in the medium was measured with a hyaluronic acid measurement kit (DuoSet Hyaluronan (R&D Systems)).

The test samples used were Examples 1 and 2 and Comparative Examples 1 to 6 as described below.

Example 1: Chicken Foot Extract Hydrolysate

The chicken foot extract hydrolysate produced in the above Production Example A was used as Example 1.

Example 2: Chicken Foot Extract Hydrolysate and N-Acetylglucosamine (GlcNAc)

A mixture of the chicken foot extract hydrolysate produced in the above Production Example A and N-acetylglucosamine (GlcNAc) (at a final concentration of 0.5 mg/mL each) was used.

Comparative Examples 1 to 6: Type I Collagen Peptide Etc.

Pig skin-derived type I collagen peptide was used as Comparative Example 1. Fish collagen was used as Comparative Example 2. Pig cartilage-derived chondroitin sulfate was used as Comparative Example 3. Salmon-derived proteoglycan was used as Comparative Example 4. A chicken comb extract was used as Comparative Example 5. N-acetylglucosamine was used as Comparative Example 6.

Results

The results are shown in Table 1. The hyaluronic acid concentration in the group without addition of the chicken foot extract hydrolysate was set at 100%, and the hyaluronic acid concentration in each of the test sample addition groups was calculated as a percentage relative to that in the group without the addition of the hydrolysate. As shown in Table 1, the relative concentration (%) of hyaluronic acid in the group with addition of the chicken foot extract hydrolysate alone (Example 1) was 350%, indicating that the hydrolysate has the effect of markedly promoting hyaluronic acid production by chondrogenic cells. On the other hand, Comparative Examples 1 to 6 showed lower relative concentrations (%) than the chicken foot extract hydrolysate group. The combination of the chicken foot extract hydrolysate and N-acetylglucosamine (GlcNAc) (Example 2) showed a relative hyaluronic acid concentration of 760%, which was higher than those in the chicken foot extract hydrolysate alone (Example 1) and in N-acetylglucosamine alone (Comparative Example 6). These results indicated that the combination of the chicken foot extract hydrolysate and N-acetylglucosamine has a synergistic effect on hyaluronic acid production.

TABLE 1

| | Test sample | Hyaluronic acid level (%) |
|---|---|---|
| Control | No sample added | 100 |
| Example 1 | Chicken foot extract hydrolysate (1 mg/mL) | 350 |
| Comparative Example 1 | Type I collagen peptide (1 mg/mL) | 80 |
| Comparative Example 2 | Fish collagen (1 mg/mL) | 140 |
| Comparative Example 3 | Chondroitin sulfate (1 mg/mL) | 60 |
| Comparative Example 4 | Proteoglycan (1 mg/mL) | 100 |
| Comparative Example 5 | Chicken comb extract (1 mg/mL) | 90 |
| Comparative Example 6 | N-acetylglucosamine (GlcNAc) (1 mg/mL) | 210 |
| Example 2 | Chicken foot extract hydrolysate + GlcNAc (at final concentration of 0.5 mg/mL each) | 760 |

Figure 2:
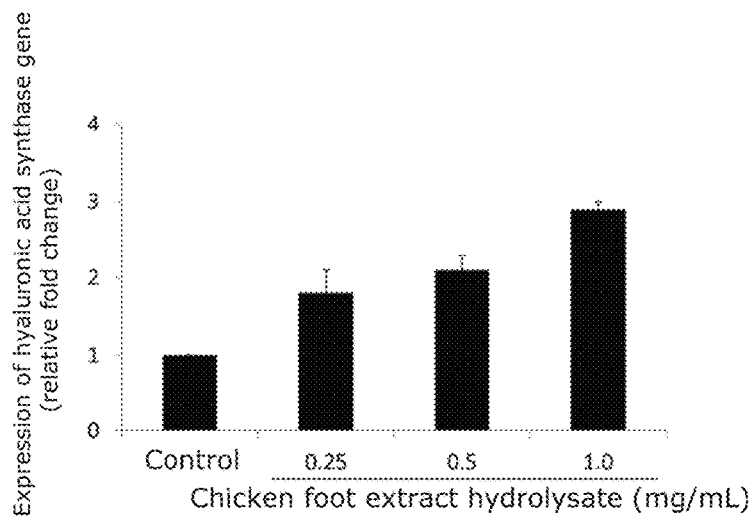
FIG. 2 shows the effect of a chicken foot extract hydrolysate on the expression of a hyaluronic acid synthase gene in chondrogenic cells.

Test Example 2: Effect of Chicken Foot Extract Hydrolysate on the Expression of Hyaluronic Acid Synthase Gene in Chondrogenic Cells Chondrogenic cells (ATDC5) at a logarithmic growth phase were suspended in medium at $2 \times 10^4$ cells/mL, and 1 mL of the suspension was added to each well of a 12-well culture plate. The cells were precultured until confluence. After all medium was removed, medium containing the chicken foot extract hydrolysate at the indicated concentrations and insulin at a final concentration of 10 μg/mL was added. After the cells were incubated for 24 hours, 500 μL/well of ISOGEN II (code No. 311-07361, NIPPON GENE Co., Ltd.) was added to recover the cells, and RNA was extracted from the recovered cells in accordance with the manual of ISOGEN II. cDNA was synthesized from the extracted RNA using Takara PrimeScript RT reagent Kit (Takara Bio, Inc.). The expression of the hyaluronic acid synthase gene (has2) in the synthesized cDNA was measured by real-time PCR (LightCycler (Roche)) using SYBR Premix Ex Taq (Takara Bio, Inc.). The results are shown in FIG. 2. The expression of the hyaluronic acid synthase gene increased in a dose-dependent manner, indicating that the chicken foot extract hydrolysate enhances the expression of the hyaluronic acid synthase gene and thereby increases the production of hyaluronic acid.

Test Example 3: Effect of Chicken Foot Extract Hydrolysate in Rabbit Osteochondral Defect Model 3-1 Test Method (1) Administration Sample The chicken foot extract hydrolysate produced in the above Production Example A was used for administration. The chicken foot extract hydrolysate was suspended in purified water at 50 mg/15 mL (50 mg/day for each animal) at the time of use. The suspension was used as an administration sample.

(2) Test Animal and Test Conditions

Rabbits (Slc:JW, male, Japan SLC, Inc.) at 22 weeks old were purchased. The purchased animals were subjected to a period of quarantine for five days, followed by a period of acclimation for seven days. The animals were kept in an animal room maintained at a temperature of 23° C. and a humidity of 55%. The animals were individually housed in an aluminum cage. The animals were fed with 120 g of solid feed (LRC4, Oriental Yeast Co., Ltd.) per day, and allowed free access to tap water as a drinking water.

(3) Preparation of Rabbit Osteochondral Defect Model

Figure 3:
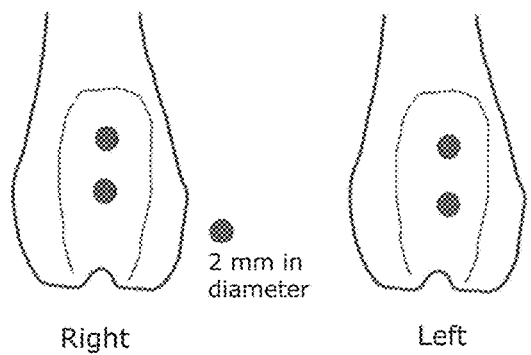
FIG. 3 shows a schematic view of circular defects created by drilling a femoral groove of a rabbit.

The animals were anesthetized by intramuscular administration of a mixed solution of ketamine hydrochloride and xylazine hydrochloride to the thigh muscle. The femoral regions were shaved, and the animals were placed supine. The shaved areas were disinfected with 5% HIBITANE (registered trademark, Sumitomo Dainippon Pharma Co., Ltd.) diluted to about 10-fold, alcohol for disinfection, and ISODINE SOLUTION 10%. Lidocaine hydrochloride in a volume of 2 to 3 mL was subcutaneously administered to the right and left thighs. The skin and fascia of the both thighs were incised with a scalpel to expose the knee joints. The incision was extended along the patellar ligament under the fascia. The joint capsule was cut to dislocate the patella. Bone defects were created on the surface of the femoral groove of each femur by drilling two holes (2 mm in diameter and 4 mm in depth) perpendicular to the bone surface (FIG. 3). During the procedure, the field of operation and the circular defects were cleaned with physiological saline (Otsuka Pharmaceutical Factory) containing enrofloxacin (0.05%). The incised fascia and skin of the right and left thighs were sutured with a suture (nylon suture, 4-0, 3-0, Alfresa Pharma Corporation). ISODINE GEL (Meiji Seika Pharma Co., Ltd.) was applied to the closed incision. After the operation, enrofloxacin was subcutaneously administered to the dorsal cervical region for two days. For prevention of infection of the incision, an Elizabethan collar was placed around the neck for one week after the operation.

(4) Group Setting and Test Schedule

Two groups, i.e., a control group (with administration of purified water) and a 50 mg/day chicken foot extract hydrolysate administration group were set up. Two rabbits were used per group and four circular defects were created per animal, that is, test was performed at n=8 (two animals per group). Oral gavage (15 mL per animal) was performed once a day for three weeks, starting from the next day of the damage development until the day before dissection. During the administration period, the general conditions and the incidence of death were observed once a day.

On the day of dissection of all animals, the animals were sacrificed by bleeding from the abdominal aorta under anesthesia by administration of 4% pentobarbital sodium into the auricular vein. The animals were dissected, and the damaged sites and their surroundings were examined macroscopically.

(5) Histopathological Analysis and Statistical Analysis

The femur (including the damaged sites) was harvested, fixed with 4% paraformaldehyde phosphate buffer, defatted, and decalcified with K-CX. The specimens were paraffin embedded in the conventional manner, and sliced into sections containing the center of the defect site. The sections were stained with HE, Alcian blue or Safranin O. For the sections stained with Alcian blue or Safranin O, the stained area was determined with a commercial software (Microsoft Office Excel 2003).

The mean and standard deviation were determined for the Alcian blue-stained area and the Safranin O-stained area in each group. The test of significance (t-test) between the control group and the chicken foot extract hydrolysate administration group was conducted. The significance level was set at 5%, and if the p-value was smaller than 5% ($p<0.05$), it was determined there was a significant difference.

3-2 Results

Figure 4:
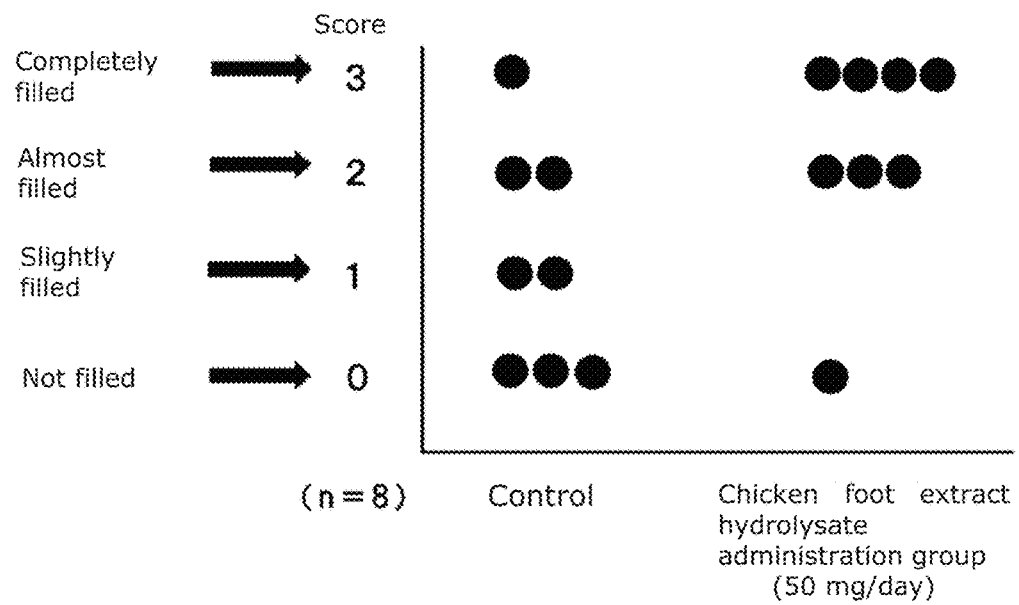
FIG. 4 shows the results of macroscopic observation of restoration of circular chondral defects after administration of 50 mg/day of a chicken foot extract hydrolysate to a rabbit for three weeks. To a control group, water was administered.

No animals died or went into a near-death state, and no abnormality was observed in the general conditions during the administration period. In the macroscopic observation at the time of dissection, the damaged sites were assessed as follows: score 0: the circular defect was not healed at all, and score 3: the circular defect was filled with cartilage matrix and the boundary of the defect became unclear (healed state), as indicated in FIG. 4. The results revealed that the restoration of the circular defects was significantly more efficient in the chicken foot extract hydrolysate administration group than in the control group.

Figure 5:
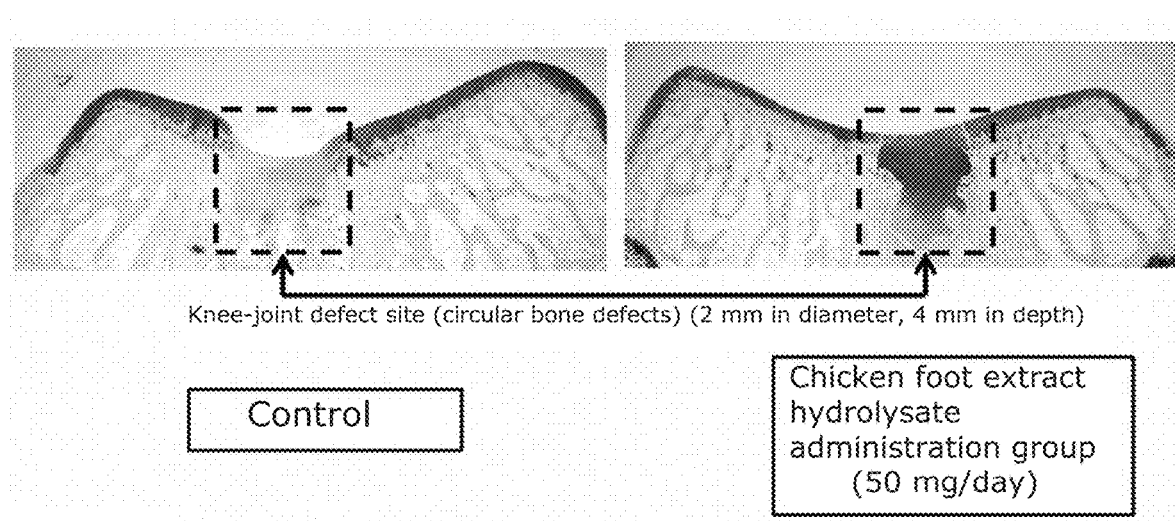
FIG. 5 shows Alcian blue-stained cartilage tissue including circular chondral defects.
Figure 6:
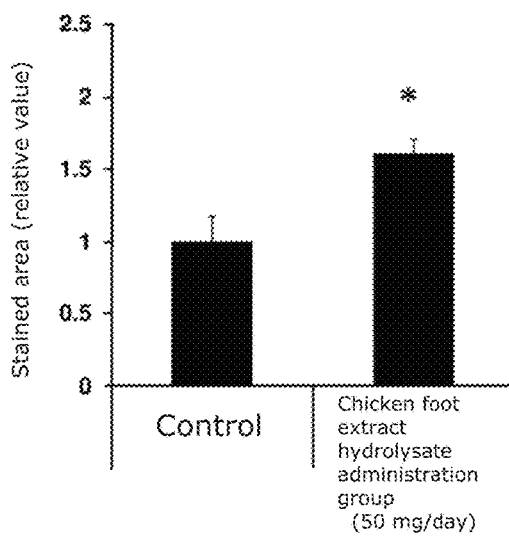
FIG. 6 is a graph showing the comparison of Alcian blue-stained area of defect sites.

For detailed analysis of the circular defects, histological sections of the bone tissue were prepared and stained with Alcian blue. As shown in FIG. 5, the circular defects of the chicken foot extract hydrolysate administration group were intensely stained. The results of measurement of the stained area of the circular defects are shown in FIG. 6. As shown in the figure, the stained area of the circular defects was significantly larger in the chicken foot extract hydrolysate administration group than in the control group. The results revealed that the cartilage matrix components, acid mucopolysaccharides, were increased by oral administration of the chicken foot extract hydrolysate.

Figure 7:
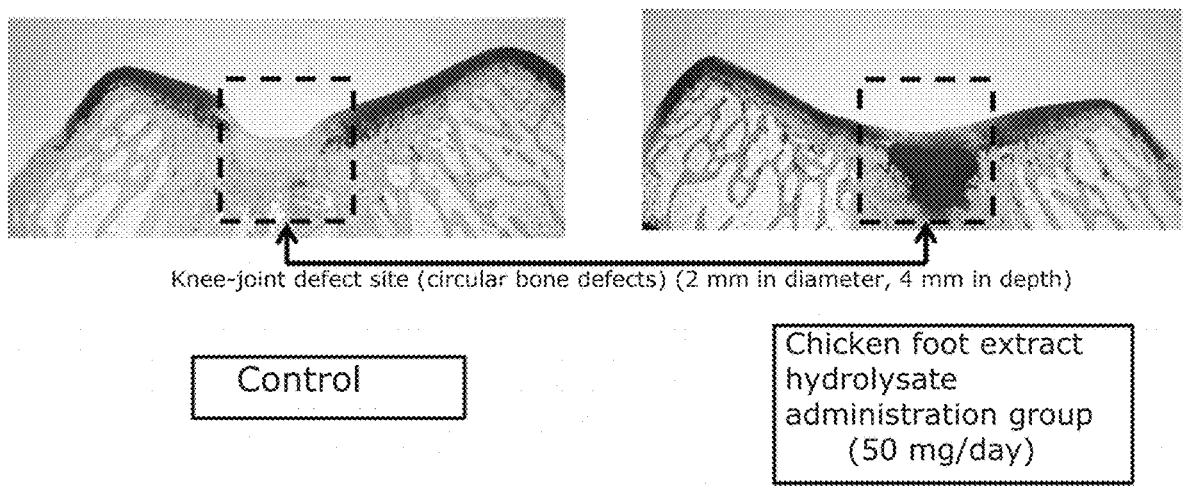
FIG. 7 shows Safranin O-stained cartilage tissue including circular chondral defects.
Figure 8:
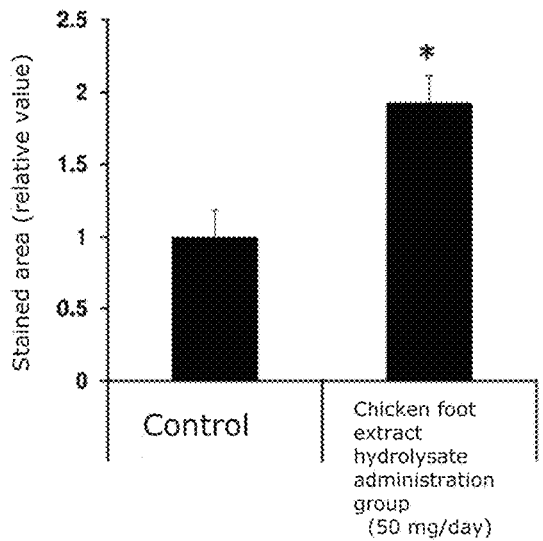
FIG. 8 is a graph showing the comparison of Safranin O-stained area.

Similarly, in Safranin O staining, the circular defects of the chicken foot extract hydrolysate administration group were intensely stained as shown in FIG. 7. The results of measurement of the stained area of the circular defects are shown in FIG. 8. As shown in the figure, the stained area of the circular defects was significantly larger in the chicken foot extract hydrolysate administration group than in the control group. The results revealed that the cartilage matrix components, proteoglycans, were increased by oral administration of the chicken foot extract hydrolysate.

Test Example 4: Verification Test of QOL Improving Effect of Capsules Containing Chicken Foot Extract Hydrolysate when Ingested by Humans Suffering from Pain in the Knee Joints 4-1 Test Method The subjects were healthy Japanese men aged between 45 and 69 and Japanese women aged between 40 and 59 who had not reached menopause, and all the subjects suffered from pain in the knee joints. The subjects were divided into groups as below. The chicken foot extract hydrolysate produced in the above Production Example A was used for administration.

Chicken foot extract hydrolysate 50 mg group: a total of 12 subjects, consisting of 5 men and 7 women at an average age of 49.8±5.9 years. One capsule contained 25 mg of the chicken foot extract hydrolysate, 223 mg of dextrin, and 2 mg of calcium stearate. The subjects ingested two capsules per day.

Chicken foot extract hydrolysate 200 mg group: a total of 12 subjects, consisting of 5 men and 7 women at an average age of 49.3±6.3 years. One capsule contained 100 mg of the chicken foot extract hydrolysate, 98 mg of dextrin, and 2 mg of calcium stearate. The subjects ingested two capsules per day.

The ingestion period of the capsules was 12 weeks. The evaluation test was performed before ingestion and 6 and 12 weeks after ingestion.

Test method: randomized, double-blind, parallel-group comparison study.

Ethical considerations: the test was performed in accordance with the Declaration of Helsinki.

4-2 Evaluation Methods
(1) WOMAC (Western Ontario and McMaster Universities Osteoarthritis Index)

WOMAC was used for the evaluation. WOMAC is a patient-reported assessment tool, in which a patient answers 24 questions about pain, stiffness (sensation of restriction), and difficulties in daily activities, and assessment is performed based on the answers. The subjects rated the assessment items on a five-point scale, including 5 items for pain, 2 items for stiffness, and 17 items for difficulties in daily activities. The rated scores were statistically analyzed. A smaller score indicates a higher QOL.

(2) JKOM (Japanese Knee Osteoarthritis Measure)

JKOM is a patient-reported QOL assessment scale specific to knee osteoarthritis in Japanese. JKOM includes the assessment of a knee pain by the VAS scale, and questions about pain and stiffness of the knee joint, difficulties in daily activities, and health conditions. VAS (Visual Analog Scale) used in this assessment is a measurement instrument for the amount of sensation that a patient feels for a particular question. The patient marks, on a 100-mm straight line, the point that he or she feels represents their perception of the current state, and the amount of sensation is determined based on the mark made by the patient. The VAS score is determined by measuring the distance from the left hand end on the line to the point that the patient marks. In JKOM, the subjects answered 25 questions on a five-point scale, including 8 items for the knee conditions, 10 items for daily activities, 5 items for going-out activities, and 2 items for health conditions. A smaller score indicates a higher QOL.

(3) SF-36

SF-36 (MOS 36-Item Short-Form Health Survey) is a subjective QOL assessment tool for health conditions. This assessment tool is widely used in various clinical fields, such as knee osteoarthritis and psychiatric disorders. SF-36 consists of 36 questions classified into nine domains: physical functioning, physical role functioning, bodily pain, general health perceptions, vitality, social role functioning, emotional role functioning, mental health, and change in health. A larger score indicates a higher QOL.

Statistical Analysis

In statistical analysis, in-group comparison was conducted by Wilcoxon signed-rank test to compare the measured values before ingestion with those at 6 and 12 weeks after ingestion. Data were considered significantly different if the critical value was 5% or less ($p<0.05$). A significant difference is indicated by a single, double or triple asterisks: * ($p<0.05$),  ($p<0.01$) and * ($p<0.001$). Inter-group comparison was conducted by Mann-Whitney U test to investigate the changes between before ingestion and 6 or 12 weeks after ingestion.

4-3 Results (in Men and Women)

Figure 9:
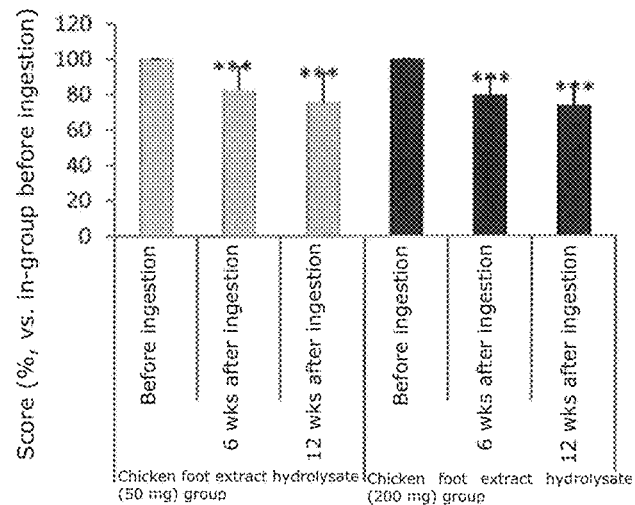
FIG. 9 shows the total score of WOMAC assessment.
Figure 10:
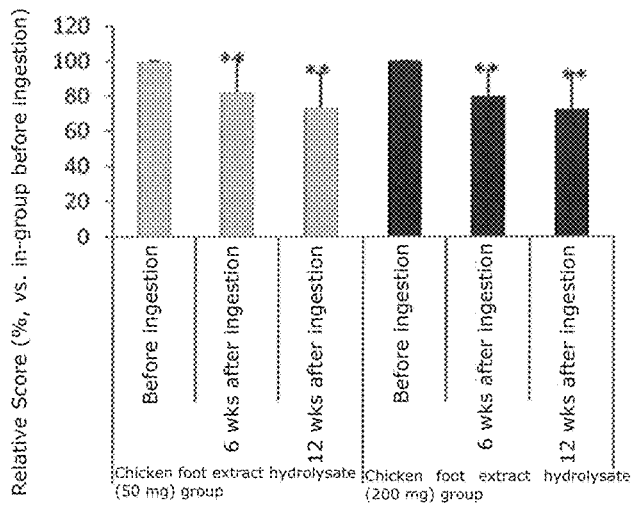
FIG. 10 shows the pain score of WOMAC assessment.
Figure 11:
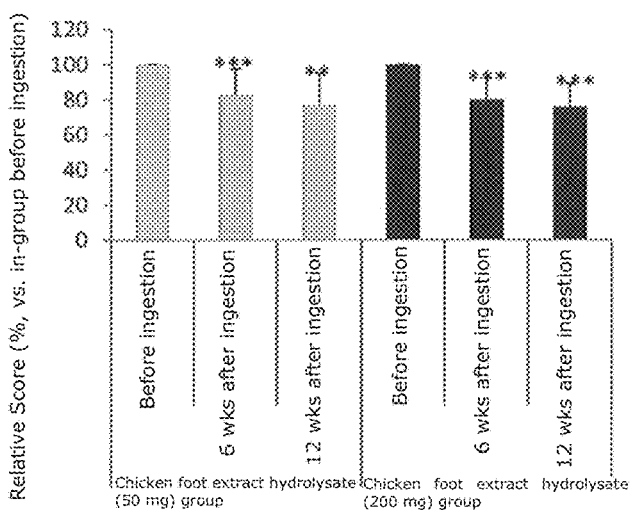
FIG. 11 shows the daily activity score of WOMAC assessment.

The results of WOMAC assessment are shown in FIGS. 9 to 11. As shown in FIG. 9, the total score was significantly reduced 6 and 12 weeks after ingestion in the chicken foot extract hydrolysate 50 mg and 200 mg groups as compared with that before ingestion, indicating the alleviation of knee joint disorders. As apparent from FIGS. 10 and 11, pain was reduced and daily activities became easier, confirming that the chicken foot extract hydrolysate is useful as an agent for improving QOL.

The results of JKOM assessment are shown in FIGS. 12 to 14. As evident from FIGS. 12 to 14, JKOM assessment also indicated that oral ingestion of the chicken foot extract hydrolysate resulted in the alleviation of knee pain and knee conditions and the reduction in the JKOM total score, indicating the improvement in QOL.

The results of SF-36 assessment are shown in FIGS. 15 and 16. As apparent from FIGS. 15 and 16, the bodily pain was reduced and physical functioning was improved by oral ingestion of the chicken foot extract hydrolysate.

The above results indicated that the chicken foot extract hydrolysate has the effects of alleviating knee pain, knee conditions and bodily pain and improving physical functioning. Also indicated is that ingestion of the chicken foot extract hydrolysate improves daily activities. Therefore, it was evident that the chicken foot extract hydrolysate is useful as an agent for improving QOL.

4-4 Results in Women

TABLE 2

| WOMAC total score | | |
|---|---|---|
| | In-group significant difference vs. before ingestion | Inter-group significant difference vs. placebo |
| Women group | Yes | Yes |
| Men group | Yes | No |

200 mg/day, 12 weeks of ingestion

The incidence rate of knee osteoarthritis in women is about 4 times higher than that in men, and accordingly high efficacy for women is desired. Women's data were sampled from the experimental data, and statistical analysis was performed. In-group comparison showed significant difference between before and after ingestion in both men and women groups. On the other hand, inter-group comparison between the hydrolysate group and the placebo group at two weeks after ingestion showed that only the women group showed significant difference in improvement in QOL, in particular, the WOMAC total score, the difficulty in daily activities and knee conditions. The analysis revealed that the chicken foot extract hydrolysate is particularly effective for women, and markedly reduces knee pain, improves daily activities and alleviates knee conditions.

Test Example 5: Verification Test of Effect of Chicken Foot Extract Hydrolysate on the Skin (1) Cell Assay (In Vitro)

Human dermal fibroblasts (HS68) were suspended in D-MEM medium [D-MEM (high glucose) (Wako Pure Chemical Industries, Ltd.) supplemented with 10% (v/v) fetal bovine serum (FBS) and 1% (v/v) penicillin-streptomycin mixed solution (Nacalai Tesque, Inc.)]. The suspension was seeded in a 24-well plate at $3 \times 10^4$ cells/well. The cells were cultured under 5% $CO_2$ at 37° C. for 24 hours. The medium was replaced with serum-free D-MEM medium [D-MEM (high glucose) (Wako Pure Chemical Industries, Ltd.) supplemented with 1% (v/v) penicillin-streptomycin mixed solution (Nacalai Tesque, Inc.)], and the chicken foot extract hydrolysate was added as a sample to the medium at 0.05 mg/mL. To a control group, no sample was added. The cells were cultured under the same conditions for 24 hours. The cells were recovered and total RNA was extracted. cDNA was synthesized from the total RNA by reverse transcription reaction. Primers for the hyaluronic acid synthase gene (has2) were added, and real-time PCR was performed using the cDNA as a template to measure the promotion of the has2 gene expression by the chicken foot extract hydrolysate.

The measurement revealed that the addition of the chicken foot extract hydrolysate at a concentration of 0.05 mg/mL significantly increased the expression level of has2 (FIG. 17).

Based on the results, it is expected that the chicken foot extract hydrolysate will enhance the expression of hyaluronic acid synthase (HAS2) in dermal cells and promote the production of hyaluronic acid, thereby increasing moisture and tension of the skin, leading to improvement in wrinkles and sagging skin.

(2) Oral Ingestion Test on Humans (In Vivo)

Based on the results of the cell assay, it was expected that the chicken foot extract hydrolysate would improve moisture and tension of the skin and wrinkles. To examine these effects, a test was carried out as described below using subjects consisting of healthy Japanese men aged between 45 and 69 and Japanese women aged between 40 and 59 who had not reached menopause, all the subjects suffering from pain in the knee joints.

A total of 12 subjects, consisting of 5 men and 7 women at an average age of 49.8±5.9 years, orally ingested two capsules per day containing the chicken foot extract hydrolysate (one capsule contained 25 mg of the chicken foot extract hydrolysate, 223 mg of dextrin, and 2 mg of calcium stearate).

The ingestion period of the capsule was 12 weeks. The evaluation test was performed before ingestion and 6 weeks after ingestion. The VAS questionnaire was used to evaluate the following items: "skin dryness", "skin tension", and "fine lines at the outer corner of the eyes". The results are shown in Table 3.

TABLE 3

Skin conditions (VAS questionnaire, n = 12)

| Item | Unit | Before ingestion | 6 weeks after ingestion of chicken foot extract hydrolysate (50 mg/day) |
|---|---|---|---|
| Skin dryness | mm | 57.5 (25.0-66.5) | 25.0** (23.0-30.3) |
| Skin tension | mm | 64.0 (49.0-67.3) | 48.5* (37.5-57.3) |
| Fine lines at outer corner of eyes | mm | 49.0 (38.5-68.0) | 31.5* (27.5-52.5) |

Median: the first quartile-the third quartile
*p < 0.05,
**p < 0.01 (Wilcoxon signed-rank test vs. before ingestion)

As apparent from Table 3, significant improvement was observed in the "skin dryness" in the chicken foot extract hydrolysate 50 mg group as compared with before ingestion ($p<0.01$). In the same group, significant improvement was also observed in the "skin tension" and the "fine lines at the outer corner of the eyes" ($p<0.05$).

The above results confirmed that the chicken foot extract hydrolysate promotes the production of hyaluronic acid in the skin, increases skin moisture, and improves skin dryness, wrinkles or skin tension.

(3) Application to Human Skin (In Vivo)

Figure 18:
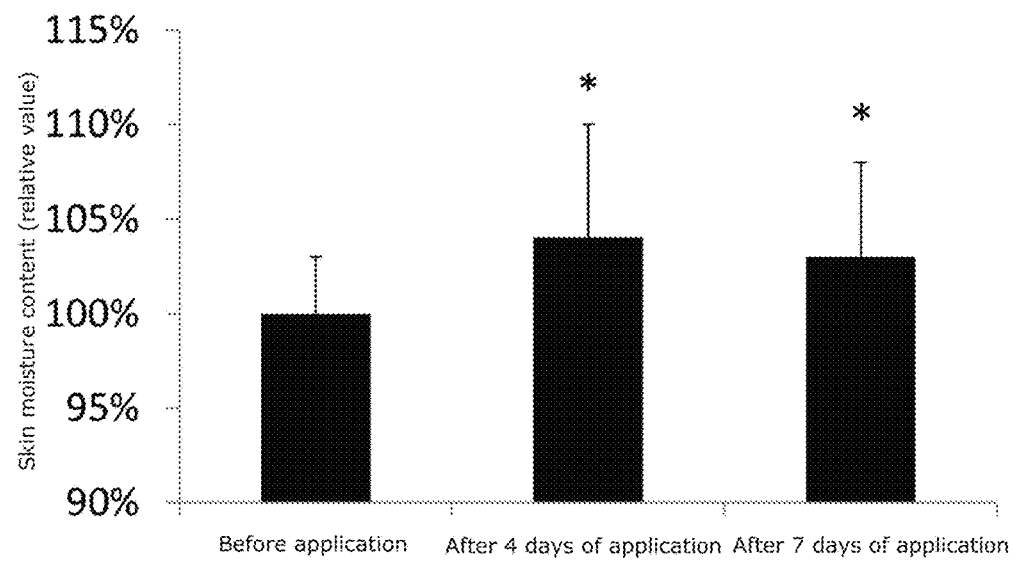
FIG. 18 is a graph showing that the application of a chicken foot extract hydrolysate improves the moisture of human skin.

To evaluate the effect of the chicken foot extract hydrolysate applied to the skin, an application test of the chicken foot extract hydrolysate to humans was performed. The subjects were a total of 10 subjects, consisting of 5 men and 5 women at an average age of 36.0 years. A 0.1% (w/v) aqueous solution of the chicken foot extract hydrolysate and a control (water) were applied to both arms in an amount of 0.05 mL for one week. The skin moisture content of the applied area was measured with Moisture Checker MY-808S (Scalar Corporation) before application and after 4 and 7 days of application. The measurement results indicated that the skin moisture content was significantly increased after 4 and 7 days of application of the solution containing the chicken foot extract hydrolysate compared with that by the application of water. The results revealed that the chicken foot extract hydrolysate increases the moisture content of the skin, which confirmed the improvement in the moisture of the skin (FIG. 18).

Production Example B: Production of a Sample (a Solution Containing Phe-Hyp Dipeptide)

A Phe-Hyp dipeptide, phenylalanyl-4-hydroxyproline, was produced by liquid-phase synthesis. The obtained Phe-Hyp dipeptide powder was dissolved in DMEM/F-12 medium to give a sample (a solution containing the Phe-Hyp dipeptide).

Test Example 6: Promoting Effect of Phe-Hyp Dipeptide on Cartilage Matrix Production by Chondrogenic Cells The mouse chondrogenic cell line ATDC5 (RIKEN BRC No. RCB0565) was cultured until subconfluence at 37° C. in an atmosphere of 5 vol % $CO_2$ and 95 vol % air in DMEM/F-12 medium supplemented with 5% (w/w) FBS, 1% (w/w) penicillin-streptomycin solution, 5 μg/mL transferrin, and $3\times10^{-8}$M sodium selenite. The cells were collected by trypsin treatment. The collected cells were suspended in fresh DMEM/F-12 medium with the same supplements as above to give a cell suspension ($50\times10^4$ cells/mL). The cell suspension was spot-seeded at a volume of 20 μL in each well of a 24-well plate, and the cells were precultured at 37° C. in an atmosphere of 5 vol % $CO_2$ and 95 vol % air for 3 hours. The medium in each well was replaced with fresh DMEM/F-12 medium containing the same supplements as above and the Phe-Hyp dipeptide (at a final concentration of 500 μM) and insulin (at a final concentration of 0.1 μg/mL), and the cells were cultured for 14 days. The cartilage matrix produced by the chondrogenic cells was stained with Alcian blue staining solution, the stained cartilage matrix was quantified with Image J (National Institutes of Health), and the results were evaluated. The amount of the cartilage matrix produced by the chondrogenic cells in the sample addition group was expressed in terms of a relative value, with the amount of the cartilage matrix in the no sample group taken as 100.

Figure 19:
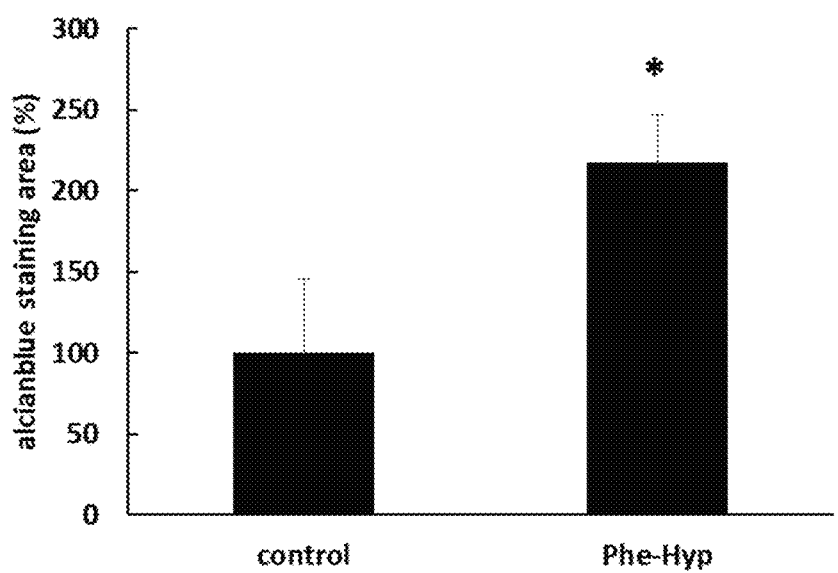
FIG. 19 is a graph showing cartilage matrix production by chondrogenic cells in the presence of a dipeptide consisting of the amino acid sequence phenylalanine-hydroxyproline (hereinafter also called a Phe-Hyp dipeptide).
Figure 20:
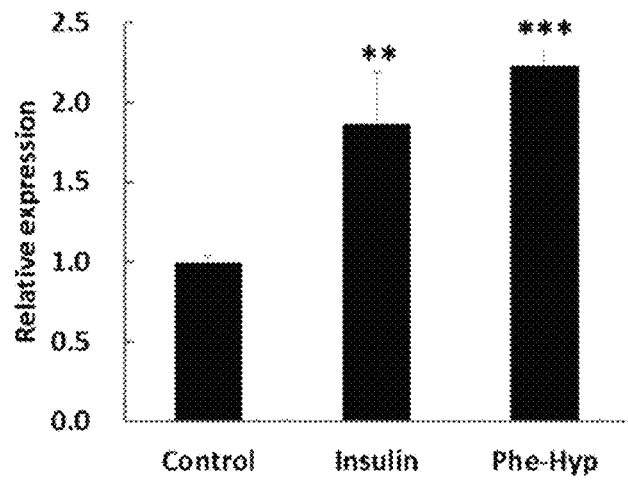
FIG. 20 is a graph showing SOX9 mRNA expression level in chondrogenic cells in the presence of a Phe-Hyp dipeptide.
Figure 21:
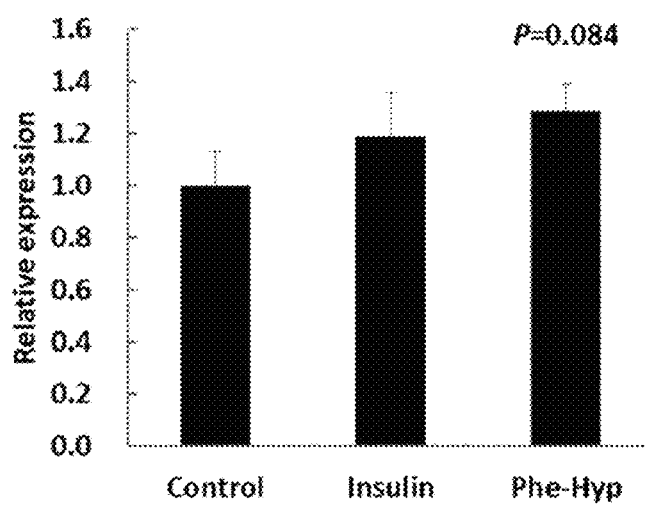
FIG. 21 is a graph showing Acan mRNA expression level in chondrogenic cells in the presence of a Phe-Hyp dipeptide.
Figure 22:
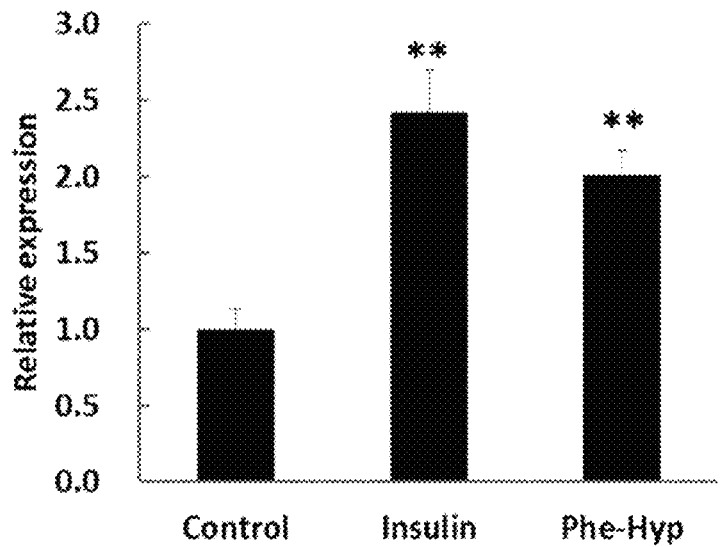
FIG. 22 is a graph showing Col X mRNA expression level in chondrogenic cells in the presence of a Phe-Hyp dipeptide.
Figure 23:
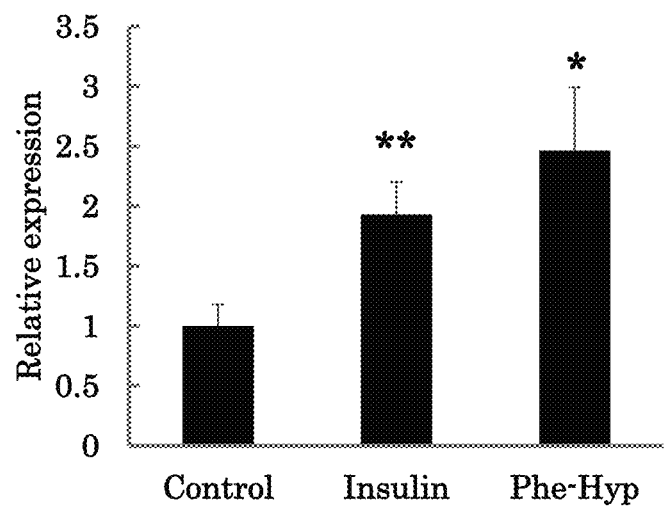
FIG. 23 is a graph showing has2 mRNA expression level in chondrogenic cells in the presence of a Phe-Hyp dipeptide.

The results are shown in FIG. 19. The Phe-Hyp dipeptide promoted cartilage matrix production by chondrogenic cells.

Test Example 7: Examination of Enhancing Effect of Phe-Hyp Dipeptide on the Expression of Cartilage Differentiation-Related Genes in Chondrogenic Cells The mouse chondrogenic cell line ATDC5 (RIKEN BRC No. RCB0565) was cultured until subconfluence at 37° C. in an atmosphere of 5 vol % $CO_2$ and 95 vol % air in DMEM/F-12 medium supplemented with 5% (w/w) FBS, 1% (w/w) penicillin-streptomycin solution, 5 μg/mL transferrin, and $3\times10^{-8}$ M sodium selenite. The cells were collected by trypsin treatment. The collected cells were suspended in fresh DMEM/F-12 medium with the same supplements as above to give a cell suspension ($10\times10^4$ cells/mL). The cell suspension was seeded at a volume of 500 μL in each well of a 24-well plate, and the cells were precultured at 37° C. in an atmosphere of 5 vol % $CO_2$ and 95 vol % air for 2 days. The medium in each well was replaced with fresh DMEM/F-12 medium containing the same supplements as above and the Phe-Hyp dipeptide (at a final concentration of 500 μM) and insulin (at a final concentration of 0.1 μg/mL), and the cells were cultured for 3 days. As a positive control, 10 μg/mL insulin was used. At end of culture, total RNA extraction and cDNA synthesis were performed, the relative mRNA expression levels of cartilage differentiation-related genes were quantified by real-time PCR and were normalized to the GAPDH mRNA expression level, and the results were evaluated. The expression levels in the sample addition groups were expressed in terms of relative fold change, with the expression levels in the no sample group taken as 1. Outliers were rejected by applying the Smirnov-Grubbs test.

The results are shown in FIGS. 20, 21, 22 and 23. The Phe-Hyp dipeptide enhanced the expression of the cartilage differentiation-related genes, SOX9, Acan, Col X and has2. *,  and * indicate the significance level at critical values of 5%, 1%, and 0.1%, respectively.

Test Example 8: Examination of Promoting Effect of Phe-Hyp Dipeptide on Ex Vivo Hyaluronic Acid Production in Knee Joints of Mice DMEM/F-12 medium supplemented with 1 mg/mL Phe-Hyp dipeptide, 5% (w/w) FBS, 1% (w/w) penicillin-streptomycin solution, 5 μg/mL transferrin, and $3 \times 10^{-8}$ M sodium selenite was added to each well of a 24-well plate at a volume of 1 mL per well. The femur and tibia were harvested from the right and left hind legs of ddY mice (female, retired). The synovial membrane was incised to expose the cartilage, and the bones were placed in each well so that only the joint was immersed in the medium. The bones were incubated at 37° C. in an atmosphere of 5 vol % $CO_2$ and 95 vol % air for one day. At end of incubation, the supernatants were recovered and centrifuged at 1500×g at 4° C. for 30 minutes. The supernatants were recovered, the amount of hyaluronic acid was measured by ELISA and the results were evaluated. The amount of the hyaluronic acid in the sample addition group was expressed in terms of a relative value, with the amount of hyaluronic acid in the no sample group taken as 100.

Figure 24:
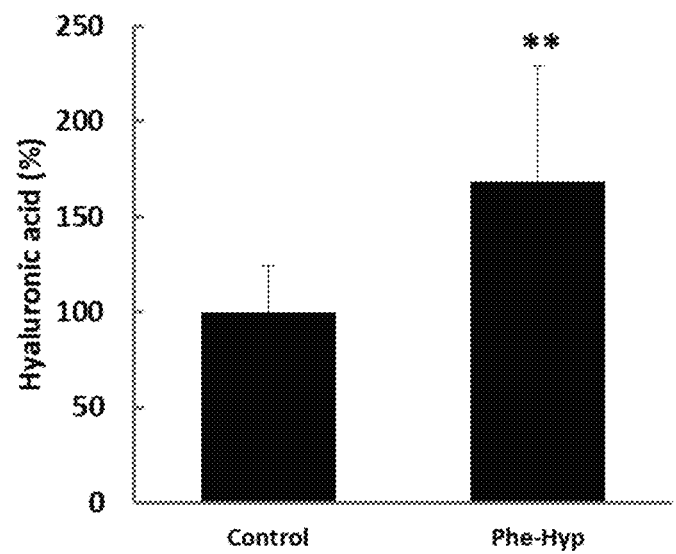
FIG. 24 is a graph showing the amount of hyaluronic acid produced in ex vivo mouse knee joints in the presence of a Phe-Hyp dipeptide.

The results are shown in FIG. 24. The Phe-Hyp dipeptide promoted ex vivo hyaluronic acid production. ** indicates the significance level at a critical value of 1%.

Example 3: Beverage

A beverage containing the chicken foot extract hydrolysate produced in the above Production Example A was prepared. Briefly, ingredients were mixed in accordance with the following formula: 15.0% by mass of saccharide isomerate, 10% by mass of fruit juice, 2.0% by mass of the chicken foot extract hydrolysate, 0.1% by mass of a flavor, 0.1% by mass of calcium and 72.8% by mass of water. The mixture was sterilized at 90° C. for 15 seconds with a plate-type pasteurizer to give a beverage.

Example 4: Yogurt

A yogurt containing the chicken foot extract hydrolysate produced in the above Production Example A was prepared. Briefly, ingredients were mixed in accordance with the following formula: 3.0% by mass of the chicken foot extract hydrolysate, 7% by mass of sucrose, 0.1% by mass of a flavor, and 89.9% by mass of a yogurt. The yogurt mixture was filled into a container.

Example 5: Cheese

A processed cheese containing the chicken foot extract hydrolysate produced in the above Production Example A was prepared. Briefly, the following ingredients were mixed: 35% by mass of Gouda cheese, 35% by mass of Cheddar cheese, 20% by mass of Parmesan cheese, 2.0% by mass of the chicken foot extract hydrolysate, 1.0% by mass of calcium phosphate, and 7.0% by mass of water. The mixture was emulsified at an emulsification temperature of 85° C. to give a processed cheese.

Example 6: Capsule

The following ingredients were mixed: 60% by mass of the chicken foot extract hydrolysate produced in the above Production Example A, 30% by mass of corn starch and 10% by mass of lactose. The mixture was filled into empty gelatin capsules (200 mg per capsule) to give capsules.

Example 7: Tablet

The following ingredients were mixed: 60% by mass of the chicken foot extract hydrolysate produced in the above Production Example A, 18% by mass of hydrogenated maltose, 18% by mass of crystalline cellulose and 4% by mass of sucrose ester. The mixture was compressed into tablets (300 mg per tablet).

Examples 8 to 12

A beverage (Example 8), a yogurt (Example 9), a cheese (Example 10), a capsule (Example 11), and a tablet (Example 12), each containing the Phe-Hyp dipeptide, were produced in the same manner as in Examples 3 to 7 except that the Phe-Hyp dipeptide produced by liquid-phase synthesis was used in place of the chicken foot extract hydrolysate.

The present invention is not limited to each of the embodiments and Examples described above, and various modifications are possible within the scope of the claims. Embodiments obtainable by appropriately combining the technical means disclosed in the different embodiments of the present invention are also included in the technical scope of the present invention.

INDUSTRIAL APPLICABILITY

The present invention is useful as a hyaluronic acid production promoting agent, in particular, a medicament, a food, a cosmetic product, a quasi-drug, or an animal feed for promoting hyaluronic acid production.

The invention claimed is:

1. A method for alleviating bodily pain by promoting hyaluronic acid production of cartilage or cartilage matrix production in a mammal, the method comprising: administering phenylalanine-hydroxyproline dipeptide, or a salt thereof, to a mammal, wherein said bodily pain is knee pain or pain associated with osteoarthritis, cartilage defects, cartilage injury or meniscus injury.

2. The method of claim 1, further comprising selecting a mammal in need of an agent that promotes hyaluronic acid production of cartilage.

* * * * *